(12) United States Patent
Becker et al.

(10) Patent No.: US 8,975,237 B2
(45) Date of Patent: Mar. 10, 2015

(54) TREATMENT OF FIBROTIC CONDITIONS

(75) Inventors: David L. Becker, Abbot Langley (GB); Colin R. Green, Auckland (NZ); Bradford James Duft, Rancho Santa Fe, CA (US)

(73) Assignee: CoDa Therapeutics, Inc., San Diego, CA (US)

( * ) Notice: Subject to any disclaimer, the term of this patent is extended or adjusted under 35 U.S.C. 154(b) by 131 days.

(21) Appl. No.: 12/809,886

(22) PCT Filed: Dec. 22, 2008

(86) PCT No.: PCT/US2008/014021
§ 371 (c)(1),
(2), (4) Date: Feb. 22, 2011

(87) PCT Pub. No.: WO2009/085270
PCT Pub. Date: Jul. 9, 2009

(65) Prior Publication Data
US 2011/0136890 A1    Jun. 9, 2011

Related U.S. Application Data

(60) Provisional application No. 61/008,795, filed on Dec. 21, 2007.

(51) Int. Cl.
A61K 48/00    (2006.01)
C07H 21/02    (2006.01)
C07H 21/04    (2006.01)

(52) U.S. Cl.
USPC ...... 514/44; 536/23.1; 536/24.31; 536/24.33; 536/24.5

(58) Field of Classification Search
None
See application file for complete search history.

(56) References Cited

U.S. PATENT DOCUMENTS

| | | | |
|---|---|---|---|
| 3,687,808 | A | 8/1972 | Merigan et al. |
| 4,861,757 | A | 8/1989 | Antoniades et al. |
| 5,034,506 | A | 7/1991 | Summerton et al. |
| 5,044,810 | A | 9/1991 | Matsuoka et al. |
| 5,166,195 | A | 11/1992 | Ecker |
| 5,998,148 | A | 12/1999 | Bennett et al. |
| 6,458,590 | B1 | 10/2002 | Mukherjee et al. |
| 6,506,559 | B1 | 1/2003 | Fire et al. |
| 6,752,987 | B1 | 6/2004 | Post et al. |
| 7,098,190 | B1 | 8/2006 | Becker et al. |
| 7,153,822 | B2 | 12/2006 | Jensen et al. |
| 7,521,191 | B2 | 4/2009 | Khvorova et al. |
| 2003/0105165 | A1 | 6/2003 | Griffith |
| 2003/0148968 | A1 | 8/2003 | Hammond et al. |
| 2003/0215424 | A1 | 11/2003 | Seul et al. |
| 2004/0092429 | A1 | 5/2004 | Jensen et al. |
| 2004/0259768 | A1 | 12/2004 | Lauermann |
| 2005/0119211 | A1* | 6/2005 | Chowrira et al. ............... 514/44 |
| 2006/0105013 | A1 | 5/2006 | Ashkar et al. |
| 2007/0232526 | A1 | 10/2007 | Kvistgaard et al. |
| 2008/0261867 | A1 | 10/2008 | Klagsbrun et al. |
| 2010/0150877 | A1 | 6/2010 | O'Brien et al. |
| 2011/0275575 | A1 | 11/2011 | Mochly-Rosen |

FOREIGN PATENT DOCUMENTS

| | | | |
|---|---|---|---|
| EP | 1 514 929 | 3/2005 | |
| JP | 2009-537229 A | 10/2009 | |
| WO | WO 96/19194 | 6/1996 | |
| WO | WO 98/24797 | 6/1998 | |
| WO | WO 00/44409 | * 8/2000 | ............. 514/44 |
| WO | WO 03/032964 A2 | 4/2003 | |
| WO | WO 03/063891 | 8/2003 | |
| WO | WO 2005/053600 A2 | 6/2005 | |
| WO | WO 2005/053600 A3 | 1/2006 | |
| WO | WO 2006/069181 A2 | 6/2006 | |
| WO | WO 2006/134494 A2 | * 12/2006 | ............. 514/44 |
| WO | WO-2007/136769 A2 | 11/2007 | |
| WO | WO 2006/134494 A3 | 5/2008 | |
| WO | WO 2008/060622 A2 | * 5/2008 | ............. 514/44 |
| WO | WO 2008/073479 A2 | 6/2008 | |
| WO | WO 2008/073479 A3 | 6/2008 | |
| WO | WO 2008/060622 A3 | 7/2008 | |
| WO | WO 2008/151022 A2 | 12/2008 | |
| WO | WO 2009/075881 A2 | 6/2009 | |
| WO | WO 2009/075881 A3 | 6/2009 | |
| WO | WO 2009/075882 A2 | 6/2009 | |
| WO | WO 2009/075882 A3 | 6/2009 | |
| WO | WO 2009/085268 A2 | 7/2009 | |
| WO | WO 2009/085269 A2 | 7/2009 | |
| WO | WO 2009/085270 A2 | 7/2009 | |
| WO | WO 2009/085271 A2 | 7/2009 | |
| WO | WO 2009/085272 A2 | 7/2009 | |
| WO | WO 2009/085273 A2 | 7/2009 | |
| WO | WO 2009/085274 A2 | 7/2009 | |
| WO | WO 2009/085275 A2 | 7/2009 | |
| WO | WO 2009/085277 A2 | 7/2009 | |
| WO | WO 2009/085268 A3 | 8/2009 | |
| WO | WO 2009/085269 A3 | 8/2009 | |

(Continued)

OTHER PUBLICATIONS

Diegelmann, et. al., "Wound Healing: An Overview of Acute, Fibrotic and Delayed Healing," Frontiers in Bioscience, 9:283-289 (Jan. 1, 2004), Irvine, CA.
Examination Report dated Jun. 12, 2013, from corresponding Australian Patent Application No. 2008343841, 4 pages.
Office Action dated Aug. 15, 2013, in corresponding Japanese Patent Application No. 2010-539513, 8 pages.
Non Final Office Action, U.S. Appl. No. 09/890,363, Mail Date Apr. 30, 2003, United States Patent Office.
Non Final Office Action, U.S. Appl. No. 09/890,363, Mail Date Jan. 6, 2004, United States Patent Office.
Non Final Office Action, U.S. Appl. No. 09/890,363, Mail Date Dec. 2, 2004, United States Patent Office.

(Continued)

*Primary Examiner* — Amy Bowman
(74) *Attorney, Agent, or Firm* — Duane Morris LLP

(57) ABSTRACT

Treatment of fibrosis and fibrotic diseases, disorders, and conditions, and associated methods, compositions, formulations and articles.

23 Claims, No Drawings

(56) References Cited

FOREIGN PATENT DOCUMENTS

| | | | |
|---|---|---|---|
| WO | WO 2009/085270 A3 | 8/2009 | |
| WO | WO 2009/085271 A3 | 8/2009 | |
| WO | WO 2009/085273 A3 | 8/2009 | |
| WO | WO 2009/085274 A3 | 8/2009 | |
| WO | WO 2009/085275 A3 | 8/2009 | |
| WO | WO 2009/097077 A2 | 8/2009 | |
| WO | WO 2009/085277 A3 | 10/2009 | |
| WO | WO 2009/148613 A1 | 12/2009 | |
| WO | WO 2009/085272 A3 | 6/2010 | |

OTHER PUBLICATIONS

Non Final Office Action, U.S. Appl. No. 11/512,735, Mail Date Feb. 7, 2008, United States Patent Office.
Non Final Office Action, U.S. Appl. No. 11/510,280, Mail Date Feb. 8, 2008, United States Patent Office.
Non Final Office Action, U.S. Appl. No. 11/447,599, Mail Date Mar. 13, 2008, United States Patent Office.
Non Final Office Action, U.S. Appl. No. 11/510,496, Mail Date Mar. 14, 2008, United States Patent Office.
Non Final Office Action, U.S. Appl. No. 11/512,728, Mail Date Mar. 17, 2008, United States Patent Office.
Non Final Office Action, U.S. Appl. No. 11/512,725, Mail Date Nov. 26, 2008, United States Patent Office.
Final Office Action, U.S. Appl. No. 11/512,735, Mail Date Nov. 26, 2008, United States Patent Office.
Non Final Office Action, U.S. Appl. No. 11/510,498, Mail Date Dec. 2, 2008, United States Patent Office.
Final Office Action, U.S. Appl. No. 11/510,280, Mail Date Dec. 11, 2008, United States Patent Office.
Non Final Office Action, U.S. Appl. No. 10/581,813, Mail Date Dec. 22, 2008, United States Patent Office.
Non Final Office Action, U.S. Appl. No. 11/447,599, Mail Date Dec. 24, 2008, United States Patent Office.
Non Final Office Action, U.S. Appl. No. 12/001,498, Mail Date Apr. 22, 2009, United States Patent Office.
Final Office Action, U.S. Appl. No. 11/512,728, Mail Date May 28, 2009, United States Patent Office.
Final Office Action, U.S. Appl. No. 11/512,725, Mail Date Aug. 27, 2009, United States Patent Office.
Final Office Action, U.S. Appl. No. 11/510,496, Mail Date Sep. 18, 2009, United States Patent Office.
Final Office Action, U.S. Appl. No. 11/447,599, Mail Date Sep. 18, 2009, United States Patent Office.
Non Final Office Action, U.S. Appl. No. 10/581,813, Mail Date Nov. 5, 2009, United States Patent Office.
Final Office Action, U.S. Appl. No. 11/510,498, Mail Date Feb. 4, 2010, United States Patent Office.
Non Final Office Action, U.S. Appl. No. 11/512,735, Mail Date Feb. 4, 2010, United States Patent Office.
Non Final Office Action, U.S. Appl. No. 12/001,498, Mail Date Apr. 1, 2010, United States Patent Office.
Non Final Office Action, U.S. Appl. No. 11/510,496, Mail Date Apr. 12, 2010, United States Patent Office.
Final Office Action, U.S. Appl. No. 10/581,813, Mail Date May 21, 2010, United States Patent Office.
Non Final Office Action, U.S. Appl. No. 11/883,739, Mail Date Sep. 16, 2010, United States Patent Office.
Final Office Action, U.S. Appl. No. 12/001,498, Mail Date Dec. 17, 2010, United States Patent Office.
Non Final Office Action, U.S. Appl. No. 12/809,974, Mail Date Feb. 4, 2011, United States Patent Office.
Non Final Office Action, U.S. Appl. No. 12/592,668, Mail Date Feb. 10, 2011, United States Patent Office.
Non Final Office Action, U.S. Appl. No. 11/883,739, Mail Date May 2, 2011, United States Patent Office.
Non Final Office Action, U.S. Appl. No. 12/592,668, Mail Date May 26, 2011, United States Patent Office.
Non Final Office Action, U.S. Appl. No. 11/447,599, Mail Date May 27, 2011, United States Patent Office.
Non Final Office Action, U.S. Appl. No. 12/812,017, Mail Date May 31, 2011, United States Patent Office.
Non Final Office Action, U.S. Appl. No. 12/812,017, Mail Date Sep. 23, 2011, United States Patent Office.
Non Final Office Action, U.S. Appl. No. 12/809,933, Mail Date Oct. 13, 2011, United States Patent Office.
Final Office Action, U.S. Appl. No. 12/809,974, Mail Date Dec. 9, 2011, United States Patent Office.
Non Final Office Action, U.S. Appl. No. 12/809,933, Mail Date Dec. 23, 2011, United States Patent Office.
Non Final Office Action, U.S. Appl. No. 12/809,989, Mail Date Jan. 4, 2012, United States Patent Office.
Final Office Action, U.S. Appl. No. 11/447,599, Mail Date Jan. 5, 2012, United States Patent Office.
Final Office Action, U.S. Appl. No. 12/592,668, Mail Date Jan. 5, 2012, United States Patent Office.
Non Final Office Action, U.S. Appl. No. 11/883,739, Mail Date Jan. 18, 2012, United States Patent Office.
Final Office Action, U.S. Appl. No. 12/812,017, Mail Date Apr. 25, 2012, United States Patent Office.
Non Final Office Action, U.S. Appl. No. 12/747,863, Mail Date Apr. 30, 2012, United States Patent Office.
Examiner's Report, Australian Application No. 21193/00, Mail Date May 2, 2003, Australian Patent Office.
Examiner's Report, Australian Application No. 21193/00, Mail Date May 25, 2004, Australian Patent Office.
Examiner's Report, Australian Application No. 2011200868, Mail Date Sep. 20, 2011, Australian Patent Office.
Examiner's Report, Australian Application No. 2011200924, Mail Date Nov. 11, 2011, Australian Patent Office.
Examiner's Report, Canadian Application No. 2361251, Mail Date Apr. 11, 2006, Canadian Patent Office.
Examiner's Report, Canadian Application No. 2361251, Mail Date Nov. 20, 2006, Canadian Patent Office.
Examiner's Report, Canadian Application No. 2361251, Mail Date Jun. 27, 2007, Canadian Patent Office.
Examiner's Report, Canadian Application No. 2361251, Mail Date Mar. 17, 2008, Canadian Patent Office.
Examiner's Report, Canadian Application No. 2361251, Mail Date Dec. 10, 2008, Canadian Patent Office.
Examiner's Report, Canadian Application No. 2361251, Mail Date Oct. 23, 2009, Canadian Patent Office.
Examiner's Report, Chinese Application No. 200680010590.X, Mail Date Jun. 27, 2011, Chinese Patent Office.
Examiner's Report, Chinese Application No. 200880126536.0, Mail Date Jul. 22, 2011, Chinese Patent Office.
Examiner's Report, Chinese Application No. 200780051207.X, Mail Date Nov. 10, 2011, Chinese Patent Office.
Examiner's Report, Chinese Application No. 200880126536.0, Mail Date Mar. 31, 2012, Chinese Patent Office.
Examiner's Report, Eurasian Application No. 200601071/28, Mail Date Jul. 19, 2007, Eurasian Patent Office.
Examiner's Report, Eurasian Application No. 201100953/26, Mail Date Dec. 21, 2011, Eurasian Patent Office.
Communication pursuant to Article 96(2) EPC, European Application No. 00901236.0, Mail Date Dec. 8, 2003, European Patent Office.
Communication, European Application No. 05016736.0, Mail Date Dec. 19, 2005, European Patent Office.
Communication pursuant to Article 94(3) EPC, European Application No. 05016736.0, Mail Date Jan. 25, 2008, European Patent Office.
Communication pursuant to Article 94(3) EPC, European Application No. 04817632.5, Mail Date Nov. 28, 2008, European Patent Office.
Communication pursuant to Rules 161 and 162 EPC, European Application No. 07853353.6-2107, Mail Date Jul. 27, 2009, European Patent Office.
Communication pursuant to Article 94(3) EPC, European Application No. 04817632.5-1212, Mail Date May 3, 2010, European Patent Office.
Communication pursuant to Article 94(3) EPC, European Application No. 06795121.0, Mail Date Jun. 6, 2010, European Patent Office.

(56) References Cited

OTHER PUBLICATIONS

Communication pursuant to Rules 161(1) and 162 EPC, European Application No. 08860470.7-2406, Mail Date Jul. 28, 2010, European Patent Office.
Communication pursuant to Rules 161(1) and 162 EPC, European Application No. 08859398.3-2405, Mail Date Jul. 28, 2010, European Patent Office.
Communication pursuant to Rules 161(1) and 162 EPC, European Application No. 08867503.8, Mail Date Aug. 9, 2010, European Patent Office.
Communication pursuant to Rules 161(1) and 162 EPC, European Application No. 08866327.3-2107, Mail Date Aug. 12, 2010, European Patent Office.
Communication pursuant to Rules 161(1) and 162 EPC, European Application No. 08867884.2-2107, Mail Date Aug. 12, 2010, European Patent Office.
Communication pursuant to Rules 161(1) and 162 EPC, European Application No. 08868841.1-2107, Mail Date Aug. 12, 2010, European Patent Office.
Communication pursuant to Rules 161(1) and 162 EPC, European Application No. 08866069.1-2107, Mail Date Aug. 23, 2010, European Patent Office.
Communication pursuant to Article 94(3) EPC, European Application No. 07853353.6-2107, Mail Date Aug. 20, 2010, European Patent Office.
Communication pursuant to Rules 161(1) and 162 EPC, European Application No. 08868457.6-2107, Mail Date Aug. 23, 2010, European Patent Office.
Communication pursuant to Rules 161(1) and 162 EPC, European Application No. 08868684.5-2107, Mail Date Aug. 23, 2010, European Patent Office.
Communication pursuant to Rules 161(1) and 162 EPC, European Application No. 09705465.4-2403, Mail Date Nov. 18, 2010, European Patent Office.
Communication pursuant to Article 94(3) EPC, European Application No. 06795121.0-2107, Mail Date Jan. 17, 2012, European Patent Office.
Communication pursuant to Article 94(3) EPC, European Application No. 08860470.7-2406, Mail Date Jan. 19, 2011, European Patent Office.
Communication pursuant to Rules 161(1) and 162 EPC, European Application No. 09758776.0-2107, Mail Date Feb. 2, 2011, European Patent Office.
Communication, European Application No. 10013180.4-2107, Mail Date Mar. 23, 2011, European Patent Office.
Communication pursuant to Article 94(3) EPC, European Application No. 04817632.5-1212, European Patent Office.
First Examination Report, Indian Application No. 1827/KOLNP/2006, Mail Date Nov. 5, 2009, Indian Patent Office.
Hearing Notice, Indian Application No. 1827/KOLNP/2006, Mail Date Dec. 12, 2011, Indian Patent Office.
First Examination Report, Indian Application No. 3287/KOLNP/2006, Mail Date Dec. 29, 2011, Indian Patent Office.
Examiner's Report, Israeli Application No. 176067, Mail Date May 17, 2009, Israeli Patent Office.
Examiner's Report, Israeli Application No. 176067, Mail Date Jun. 17, 2010, Israeli Patent Office.
Examiner's Report, Japanese Application No. 2000-595711, Mail Date Aug. 31, 2010, Japanese Patent Office.
Examiner's Report, Japanese Application No. 2006-542058, Mail Date Apr. 20, 2012, Japanese Patent Office.
Examination Report, New Zealand Application No. 513154, Mail Date May 23, 2002, New Zealand Patent Office.
Examination Report, New Zealand Application No. 548204, Mail Date Jan. 30, 2008, New Zealand Patent Office.
Examination Report, New Zealand Application No. 561098, Mail Date Mar. 17, 2009, New Zealand Patent Office.
Examination Report, New Zealand Application No. 578734, Mail Date Aug. 5, 2009, New Zealand Patent Office.
Examination Report, New Zealand Application No. 577673, Mail Date Jul. 20, 2010, New Zealand Patent Office.
Examination Report, New Zealand Application No. 588010, Mail Date Sep. 17, 2010, New Zealand Patent Office.
Examination Report, New Zealand Application No. 590937, Mail Date Feb. 10, 2011, New Zealand Patent Office.
Examination Report, New Zealand Application No. 597736, Mail Date Jan. 24, 2012, New Zealand Patent Office.
Examination Report, New Zealand Application No. 597900, Mail Date Feb. 7, 2012, New Zealand Patent Office.
Examination Report, New Zealand Application No. 598866, Mail Date Mar. 19, 2012, New Zealand Patent Office.
Official Action, Russian Application No. 2009126594, Mail Date Mar. 14, 2012, Russian Patent Office.
Notification, Russian Application No. 2009126594, Mail Date Nov. 11, 2011, Russian Patent Office.
Official Action, Russian Application No. 2009122370, Mail Date Mar. 16, 2012, Russian Patent Office.
Invitation to Respond to Written Opinion, Singaporean Application No. 200705664-1, Mail Date May 27, 2009, Singaporean Patent Office.
International Preliminary Examination Report, PCT Application No. PCT/GB00/00238, Mail Date Apr. 4, 2011, World Intellectual Property Office.
International Search Report, PCT Application No. PCT/GB00/00238, Mail Date Jun. 19, 2000, World Intellectual Property Office.
International Search Report, PCT Application No. PCT/US09/003408, Mail Date, Nov. 23, 2009, World Intellectual Property Office.
International Search Report, PCT Application No. PCT/US09/00129, Mail Date Nov. 13, 2009, World Intellectual Property Office.
Singaporean Search Report, Singaporean Application No. 200603748-5, Mail Date Dec. 8, 2011, Danish Patent & Trademark Office.
Written Opinion of the International Searching Authority, PCT Application No. PCT/US08/013655, Mail Date Jul. 31, 2007, World Intellectual Property Office.
Written Opinion of the International Searching Authority, PCT Application No. PCT/US09/003408, Mail Date Dec. 4, 2010, World Intellectual Property Office.
Written Opinion of the International Searching Authority, PCT Application No. PCT/US08/014023, Mail Date Jun. 21, 2010, World Intellectual Property Office.
Written Opinion of the International Searching Authority, PCT Application No. PCT/US09/000129, Mail Date Jul. 7, 2010, World Intellectual Property Office.
Written Opinion of the International Searching Authority, PCT Application No. PCT/US08/014019, Mail Date Jun. 21, 2010, World Intellectual Property Office.
Written Opinion of the International Searching Authority, PCT Application No. PCT/US08/014024, Mail Date Jun. 21, 2010, World Intellectual Property Office.
Written Opinion of the International Searching Authority, PCT Application No. PCT/US08/014022, Mail Date Jun. 21, 2010, World Intellectual Property Office.
Written Opinion of the International Searching Authority, PCT Application No. PCT/US08/014020, Mail Date Jun. 21, 2010, World Intellectual Property Office.
Written Opinion of the International Searching Authority, PCT Application No. PCT/US08/014026, Mail Date Jun. 21, 2010, World Intellectual Property Office.
Written Opinion of the International Searching Authority, PCT Application No. PCT/US08/014021, Mail Date Jun. 21, 2010, World Intellectual Property Office.
Written Opinion of the International Searching Authority, PCT Application No. PCT/US08/013656, Mail Date Jun. 11, 2010, World Intellectual Property Office.
Written Opinion of the International Searching Authority, PCT Application No. PCT/US07/025446, Mail Date Jun. 11, 2009, World Intellectual Property Office.
Written Opinion of the International Searching Authority, PCT Application No. PCT/US07/024085, Mail Date May 15, 2009, World Intellectual Property Office.

(56) References Cited

OTHER PUBLICATIONS

Written Opinion of the International Searching Authority, PCT Application No. PCT/IB04/004431, Mail Date Jun. 3, 2006, World Intellectual Property Office.
Written Opinion of the International Searching Authority, PCT Application No. PCT/IB06/001961, Mail Date May 23, 2008, World Intellectual Property Office.
Written Opinion of the International Searching Authority, PCT Application No. PCT/US08/014025, Mail Date Jun. 21, 2010, World Intellectual Property Office.
Written Opinion of the International Searching Authority, PCT Application No. PCT/US08/014028, Mail Date Jun. 21, 2010, World Intellectual Property Office.
Wound-healing technology shortlisted for award. UCL News. University College London. Sep. 27, 2006 http://www.ucl.ac.uk/news-archive/archive/2003/october-2003/latest/newsitem.shtml?0309 . . . .
Welcome to the lab of David Becker and Jeremy Cook. Becker/Cook Lab. May 26, 2006 http://www.anat.ucl.ac.uk/research/becker/people.htm.
Nice blurb on biologics on cbsnews.com. Laxat. Sep. 9, 2006 http://www.laxat.com/Nice-blurb-on-biologics-on-cbsnews-com-1219610.html.
News bio-active gel cuts wound heeling time in half. Oct. 20, 2003. UCL Media Relations. University College London. Sep. 29, 2006 http://www.ucl.ac.uk/media/library/nexagon0.
Medical Futures—Innovation Awards. May 26, 2006 http://www.medicalfutures.co.uk/runner.php?txtWin=1.
Janes, Andrew. "Speed healing." Dec. 1, 2004. Issue 67. Unlimited. Sep. 29, 2006 http://unlimited.co.nz/unlimited.nsf/ulfuture/250EA628CE599A70CC256F6B00046325.
Hall, Celia. "Gel is helping wounds heal in half the time." Telegraph UK. Oct. 20, 2003. http://www.telegraph.co.uk/news/main.jhtmil?xml=/news/2003/10/20/nge120.xml&sSheet=. . . .
Collaborative Neuroscience the Spinal Cord Injury Project. Care Cure Community Postings for "Gel 'is helping wounds heal in half the time'/nexagon." Sep. 29, 2006 http://sci.rutgers.edu/forum/showthread.php?t=6653.
BBC News "Gels heal wounds more quickly"; http://news.bbc.co.uk/1/hi/health/3243633.stm. (May 26, 2006).
Bashyam, Hema. "Scar-free healing." (Jan. 7, 2008) JEM 205(1):2-3.
Adwan, et. al. "Downregulation of osteopontin and bone sialoprotein II is related to reduced colony formation and metastasis formation of MDA-MB-231 human breast cancer cells." Cancer Gene Therapy (2004) 11:109-120. Nature Publishing Group.
Agrawal, et. al. "Antisense Oligonucleotides, towards clinical trials." Protocols for Oligonucleotides and Analogs, Synthesis and Properties Human Press Inc., "Antisense Oligonucleotides, towards clinical trials." New Jersey. 1993.
Aitken, et. al. "Adenoviral Down-Regulation of Osteopontin Inhibits Human Osteoclast Differentiation In Vitro." Journal of Cellular Biochemistry (2004) 93:896-903. Wiley-Liss, Inc.
Baldwin, et. al. "Growth factors in corneal wound healing following refractive surgery: A Review" (Jun. 2002) ACTA Ophthalmologica Scandinavica 80(3):2002-06.
Becker, et. al. Cell coupling in the retina: Patterns and purpose. (1998) Cell Biol. Int. 22, 781-792.
Becker, et. al. Connexin alpha1 and cell proliferation in the developing chick retina. Expl. Neurol. (1999) 156(2): 326-332.
Becker, D.L., Bonness, V., Catsicas, M. and Mobbs, P. (2002) Changing patterns of ganglion cell coupling and connexin expression during chick retinal development. J. Neurobiol. 52, 280-293.
Becker, et. al. Expression of major gap junction connexin types in the working myocardium of eight chordates. (1998) Cell Biol. Int. 22, 527-543.
Becker, et. al. Functional analysis of amino acid sequences in connexin 43 involved in intercellular communication through gap junctions. (1995) J. Cell Sci. 108, 1455-1467.
Becker, D.L., Evans, W.H., Green C.R. and Warner, A.E. (1995) Functional block of gap junctional communication using antipeptide antibodies: Molecular localization of the putative binding sites. Intercellular communication through gap junctions: Ed. Y. Kanno. Progress in Cell Research, 4; 427-430.
Becker DL, Green CR (2001) Gap junction-mediated interactions between cells. Chapter 3 In Cell-Cell Interactions—A Practical Approach ed. TP Fleming. Oxford University Press, pp. 47-70.
Becker, D.L., Lin, J.S. and Green G.R. (1999) Pluronic gel as a means of antisense delivery. In Antisense techniques in the CNS. A practical approach, Eds. R. Leslie, A.J. Hunter and H.A. Robertson. pp. 149-157.
Becker, D.L., McGonnell, I., Makarenkova, H., Patel, K., Tickle, C., Lorimer, J., and Green, C.R. (1999) Roles for alpha1 connexin in morphogenesis of chick embryos using a novel antisense approach. Dev. Genetics. 24, 33-42.
Becker, D.L. and Davies, C.S. (1995) The role of gap junctions in the development of the preimplantation mouse embryo. In Microscopy of Intercellular Communicating Junctions. Ed. R. Gourdie. Microsc. Res. Tech. 31, 364-374.
Becker, D.L., David-Leclerc, C. and Warner A.E. (1992) the relationship of gap junctions and compaction in the preimplantation mouse embryo. Development Suppl., 113-118.
Becker, D.L., Ciantar, D., Catsicas, M., Pearson, R. and Mobbs, P. (2002) Use of pIRES vectors to express EGFP and connexin constructs in studies of the role of gap junctional communication in the early development of the chick retina and brain. Cell Commun. Adhes. 8, 355-359.
Behrend, et. al. "Reduced Malignancy of ras-transformed NIH 3T3 Cells Expressing Antisense Osteopontin RNA." Cancer Research (Feb. 1, 1994) 54:832-837.
Bork, et. al. "Powers and Pitfalls in Sequence Analysis: The 70% Hurdle." Genome Research (2000) 10:398:400. Cold Spring Harbor Laboratory Press.
Bork, et. al. "Protein annotation: detective work for function prediction." (Jun. 1998) TIG 14(6): 248-250. Elsevier Science Ltd.
Branch, et. al. "A good antisense molecule is hard to find." TIBS (Feb. 1998) 23:45-50. Elsevier Science Ltd.
Brandner, et. al., "Connexins 26, 30, and 43: Differences Among Spontaneous, Chronic, and Accelerated Human Wound Healing." J. Invest Dermatol. 122:1310-20 (2004).
Brenner, et. al. "Errors in genome annotation." Trends in Genetics. (1999) 15(4):132-133. Elsevier Science.
Celetti, et. al. "Overexpression of the Cytokine Osteopontin Identifies Aggressive Laryngeal Squamous Cell Carcinomas and Enhances Carcinoma Cell Proliferation and Invasiveness." (2005) Clinical Cancer Res 11(22):8019-8027. AACR Journals.
Cooper, et.al. "Wound healing and inflammation genes revealed by array analysis of macrophageless PU.I null mice." Genome Biology (2004) 6(I): Article 5.
Cotrina, et. al. "Astrocytic gap junctions remain open during ischemic conditions." (Apr. 1, 1998) J. Neurosci., 18:2520-2537.
Cotter, et. al. "Pulmonary edema: new insight on pathogenesis and treatment." (2001) Current Opinion in Cardiology. 16:159-163. Lippincott Williams & Wilkins, Inc.
Coutinho, et. al. "Limiting burn extension by transient inhibition of Connexin43 expression at the site of injury." (2005) British Journal of Plastic Surgery 58:658-667. Elsevier.
Database Geneseq, Dec. 28, 2007, "Viral regulatory miRNA Seq Id No. 263327" Retrieved from EBI accession No. GSN: AJK11008.
Database Geneseq, Dec. 28, 2007, "Viral regulatory miRNA Seq Id No. 286128" Retrieved from EBI accession No. GSN AJK33809.
Database EMBL, Jul. 9, 2006, "Rattus norvegicus piRNA piR-152346, complete sequence." Retrieved from Ebi accession No. EMBL: DQ737024.
STN Biosis Caesar accession No. 1231, Bilska, Grazul, (Aug. 8-11, 1998), "Transfection of bovine luteal cells with gap junctional protein connexin 43 (Cx43) antisense oligonucleotide affects progesterone secretion." AN 1998:379610.
STN Biosis Caesar accession No. 1233. Moore, Lisa. (1995)"Selective block of gap unction channel expression with connexin-specific antisense oligodeoxynucleotides." AN 1995:31398.
Dang, et. al. "The carboxy-tail of connexin-43 localizes to the nucleus and inhibits cell growth." Molecular and Cellular Biochemistry (2003) 242:35-38. Kluwer Academic Publishers. Netherlands.

(56) References Cited

OTHER PUBLICATIONS

Davis, et al. "Modulation of Connexin43 Expression: Effects on Cellular Coupling" Journal of Cardiovascular Electrophysiology, Futura Publishing Co., (1995) 6(2):103-114.

Diegelmann, et. al. "Wound Healing: An Overview of Acute, Fibrotic and Delayed Healing." (Jan. 1, 2004) Frontiers in Bioscience 9:283-289. Irvine, CA.

Doerks, et. al. "Protein annotation: detective work for function prediction." (1998) Trends in Genetics 14(6):248-250. Elsevier Science Ltd.

Dublin, et. al. "Satellite glial cells in sensory ganglia: Their possible contribution to inflammatory pain." (2007) Brain, Behaviior, and Immunity 21:592-598. Elsevier Inc.

Evans, et. al. "Connexin mimetic peptides: specific inhibitors of gap junctional intercellular communication." (2001) Biochem. Soc. Trans. 29:606-612. Biochemical Society.

Evans, et. al. "Design of Nonpeptidal Ligands for a peptide receptor: cholecystokinin antagonists." (1987) J. Med. Chem. 30:1229. American Chemical Society.

Frantseva, M., et al. "Ischemia-Induced Brain Damage Depends on Specific Gap-Junctional Coupling." (2002) Journal of Cerebral Blood Flow and Metabolism, 22:453-462. Lippincott Williams & Wilkins, Inc. Philadelphia.

Giaume, et. al. "Control of gap junctional communication in astrocytic networks." (1996) TINS, 19,319-325. Elsevier Science Ltd.

Goliger, et. al. "Wounding alters epidermal connexin expression and gap junction-mediated intercellular communication." (Oct. 1995) Molecular Biology of the Cell 6:1491-1501. The American Society for Cell Biology.

Gourdie, et. al. "Evidence for a distinct gap-junctional phenotype in ventricular conduction tissues of the developing and mature avian heart." Circ Res. (Feb. 1993);72(2):278-89.

Gourdie, et. al. "Immunolabelling patterns of gap junction connexins in the developing and mature rat heart." (1992) Anat Embryol (Berl) 185(4):363-78.

Gourdie, et. al. "The spatial distribution and relative abundance of gap-junctional connexin40 and connexin43 correlate to functional properties of components of the cardiac atrioventricular conduction system." (1993) Journal of Cell Science 105, 985-991. The Company of Biologist Limited 1993. Great Britain.

Gourdie, et. al. "Gap junction distribution in adult mammalian myocardium revealed by an anti-peptide antibody and laser scanning confocal microscopy." (May 1991) J Cell Sci.;99 (Pt 1):41-55. The Company of Biologist Limited 1993. Great Britain.

Gourdie, et. al. Cardiac gap junctions in rat ventricle: localization using site-directed antibodies and laser scanning confocal microscopy, Abstract. (1990) Cardioscience. (1):75-82. PMID: 1966373.

Gourdie, et. al. "The Unstoppable Connexin43 Carboxyl-Terminus" (2006) Ann. N.Y. Acad. Sci. 1080:49-62. New York Academy of Sciences.

Grazul-Bilska, et al. "Transfection of bovine luteal cells with gap junctional protein connexin 43(Cx43) antisense oligonulciotide affects progesterone secretion." (Jun. 1998) Abstract, Biology Reproduction, 58(6):78.

Green, et. al. "Analysis of the rat liver gap junction protein: clarification of anomalies in its molecular size." (1988) Prot. R. Soc. Lond. B 233:165-174. Printed in Great Britain.

Green, et. al. "Connexon rearrangement in cardiac gap junctions: evidence for cytoskeletal control?" (1984) Cell Tissue Res. 237(1):185-6. Spinger-Verlag.

Green, et. al. Distribution and role of gap junctions in normal myocardium and human ischaemic heart disease. (Feb. 1993) Histochemistry. 99(2):105-20. Springer-Verlag.

Green, et. al. Expression of the connexin43 gap junctional protein in tissues at the tip of the chick limb bud is related to the epithelial-mesenchymal interactions that mediate morphogenesis. (Jan. 1994) Dev Biol. 161(1):12-21. Academic Press, Inc.

Green, et. al. "Evidence mounts for the role of gap junctions during development." (Jan. 1998) Bioessays. 8(1):7-10.

Green, et. al. "Gap junction connexon configuration in rapidly frozen myocardium and isolated intercalated disks." (Aug. 1984) J Cell Biol. 99(2):453-63.

Green, et. al. "Spatiotemporal depletion of connexins using antisense oligonucleotides. Techniques in the study of gap junctions." (2001) Connexin methods and protocols 154 175-185. Eds R. Bruzzone and C. Giuame. Humana Press. Totowa, New Jersey.

Green, et. al. Validation of immunohistochemical quantification in confocal scanning laser microscopy: a comparative assessment of gap junction size with confocal and ultrastructural techniques. (Sep. 1993 ) J Histochem Cytochem. 41 (9):1339-49. The Histochemical Society, Inc. U.S.A.

Herve, et. al. "Diversity in protein-protein interactions of connexins: emerging roles." (2004) Biochimica et Biophyusica Acta 1662:22-41. Elsevier B.V.

Herbertt, et. al. "Protein Kinase C a Expression is required for heparin inhibition of rat smotth muscle cell proliferation in vitro and in vivo." (Oct. 18, 1996) J Biol Chem. 271(42):25928-35. The American Society for Biochemistry and Molecular Biology, Inc. U.S.A.

Hodgins, M., et. al. "Connecting Wounds with Connexins" (2004) J. Invest. Dermatol. 122:(5):ix-x commentary. The Society for Investigative Dermatology, Inc.

Ilvesaro, et. al. "Connexin-mimetic peptide Gap 27 decreases osteoclastic activity." (Dec. 5, 2001) BMC Musculoskeletal Disorders 2:10-15.

Hunter, et. al. "Zonula occludens-1 alters connexin43 gap junction size and organization by influencing channel accretion." (Dec. 2005) Molecular Biology of the Cell 16:5686-5698. The American Society for Cell Biology.

Jackowski, et. al. "Neural injury repair: hope for the future as barriers to effective CNS regeneration become clearer." (1995) British Journal of Neurosurgery 9:303-317. The Neurosurgical Foundation.

Jen, et al., "Suppression of gene expression by targeted disruption of messenger RNA: Available Options and Current Strategies." (2000) Stem Cells 18:307-319. AlphaMed Press.

Johnsson, et. al. (1999) "Hyaluronidase ameliorates rejection-induced edema."Springer-Verlag.

Johnson, et. al. "Etiology and treatment of macular edema." (Jan. 2009) Macular Edema. 147(1):11-22). Elsevier Inc.

Kaal, et. al. "The management of brain edema in brain tumors." (2004). Current Opinion in Oncology 16:593-600. Lippincott Williams & Wilkins.

Kandyba, et. al. "A murine living skin equivalent amenable to live cell imaging: analysis of the roles of connexins in the epidermis.". (Apr. 2008) The Society for Investigative Dermatology.

Landau, et. al. (1995) "Intrapericardial basic fibroblast growth factor induces myocardial angiogenesis in a rabbit model of chronic ischemia." American Heart Journal 129(5):924-931. Mosby-Year Book, Inc.

Law, et. al. "In vitro optimization of antisense ologodeoxynucleotide design: an example using the connexin gene family." Journal of Biomolecular techniques. (Sep. 2006) 17(4):270-282.

Liaw, et. al. "Altered wound healing in mice lacking a functional osteopontin gene (spp1)" (Apr. 1998) The Journal of Clinical Investigation 101(7):1468-1478.

Lin, et. al. "Gap-junction-mediated propagation and amplification of cell injury." (Oct. 1998) Nature Neurosci., 1(6):494-500.

Lw, et. al. "v-Src phosphorylation of connexin 43 on Tyr247 and Tyr265 disrupts gap junctional communication." (Aug. 20, 2001) Journal of Cell Biology. 154:815-827. The Rockefeller University Press.

Liu, et. al. "The Inhibition of in vivo tumorigenesis of osteosarcoma (OS)-732 Cells by antisense human osteopontin RNA." (2008) 13:11-19. University of Wroclaw, Poland.

Lemanske, et. al. "Asthma". (2003) J Allergy Clin Immunol 111(2): S502-S519. Mosby, Inc.

Marmarou, A. "A review of progress in understanding the pathophysiology and treatment of brain edema." (2007) Neurosurg Focus 22(5):E1.

Mattu, et. al. "Modern management of cardiogenic pulmonary edema." (2005) Emerg Med Clin N Am 23:1105-1125. Elsevier Saunders.

(56) References Cited

OTHER PUBLICATIONS

Miyazaki, et. al. "Corneal Wound Healing in an Osteopontin-Deficient Mouse." (Apr. 2008) Investigative Ophthalmology & Visual Science 49(4):1367-1375. Association for Research in Vision and Ophthalmology.

Moore, et. al. "Selective block of gap junction channel expression with connexin-specific antisense oligodeoxynucleotides." Am. J. Physiology. 265(1):C1371-C1388 (1994) The American Physiological Society.

Mori, et al., "Acute downregulation of connexin43 at wound sites leads to a reduced inflammatory response, enhanced keratinocyte proliferation and wound fibroblast migration." Journal of Cell Science. 119(24):5193-5203 (Dec. 2006). The Compny of Biologists 2006.

Mori, et al., Supplemental Materials and Methods. Online Supplemental Material. (2008) http://www.jem.org/cgi/content/full/jem.20071412/DC1 JEM The Rockefeller University Press.

Mori, et al., "Impairment of skin wound healing in b-1, 4-galactosyltransferase-deificient mice with reduced leukocyte recruitment." American Journal of Pathology (Apr. 2004) 164(4): 1303-1314. American Society for Investigative Pathology.

Muramatsu, et al., "Inhibition of osteopontin expression and function in oral cancer cell lines by antisense oligonucleotides." (2005) Cancer Letters 217:87-95. Elsevier.

Nakano, et al., "Changes in the expression of the gap junction protein connexin43 during wound healing of the rat corneal endothelium." (Dec. 2004) Bioimages 12(2-4). Bioimaging Society.

Neckers, et al., "Anti-sense technology: biological utility and practical considerations." (1993) Am. J. Physiol. 265:L1-L12.

Ngo, et al., Computational complexity, protein structure prediction, and the levinthal paradox. (1994) Tertiary Structure Prediction, pp. 492-495. Editors K Merz, Jr. and S. Le Grand. Birkhauser. Boston.

Okada, et al., "Osteopontin expressed by renal tubular epithelium interstitial monocyte infiltration in rats." Am Physiol Renal Physiol. (2000) 278:F110-F121. The American Physiological Society.

Oviedo-Orta et al., Gap junctions and connexins: potential contributors to the immunological synpase. J Leuk Bioi (2002) 72: 636-642. Elsevier.

Oviedo-Orta, et al., "Gap junctions and connexin-mediated communication in the immune system." (2004) Biochemica et Biophysica Acta 1662:102-112. Elsevier.

Papangelou, et al., "Pharmacologic Management of brain edema." (2009) Curr Treatment Options in Neural 11:64-73. Current Medicine Group LLC.

Qiu, et al; "Targeting Connexin43 Expression Accelerates the Rate of Wound Repair"; Current Biology, Current Science, GB, vol. 13, No. 19, Sep. 30, 2003, pp. 1697-1703. Elsevier Science Ltd.

Qiu, et al; "Supplemental Data: Targeting Cormexin43 Expression Accelerates the Rate of Wound Repair"; 2003 S1.

Rabinstein, A. "Treatment of Cerebral Edema." (Mar. 2006) The Neurologist 12(2):59-73.

Ratkay-Traub, et al., "Regenaration of rabbit cornea following excimer laser photorefractive keratectomy: A study on gap junctions, epithelial junctions and epidermal growth factor receptor expression in correlation with cell proliferation." Experimental Eye Research, 73(3):Sep. 2001. Academic Press.

Rhett, et al., "Novel therapies for scar reduction and regenerative healing of skin wounds." (Mar. 4, 2008). Trends in Biotechnology. 26(4): 173-180. Cell Press.

Rozenthal, et al., "Stable Transfection With Connexin43 Inhibits Neuronal Differentiation of PC12 Cells" (Oct. 25, 1997) Society for Neuroscience Abstracts, Society for Neuroscience 23(1-3), p. 22.

Ruch, et al., "Inhibition of Gap Junctional intercellular communication and enhancement of growth in BALB/c 3T3 cells treated with connexin43 antisense oligonucleotides." Molecular Carcinogenesis, (Dec. 14, 1995) 4: 269-274. Wiley-Liss, Inc.

Saez, et al., "Plasma membrane channels formed by connexins: their regulation and functions." (2003) Physiol Rev 83:1359-1400. The American Physiological Society.

Santoro, S.W. et al., "A General Purpose RNA-Cleaving DNA Enzyme." Proc. Natl. Acad. Sci. USA 94, 4262-4266 (1997). The National Academy of Sciences of the USA.

Schumacher, et al., Induction of neoangiogenesis in ischemic myocardium by human growth factors: first clinical results of a new treatment of coronary heart disease. (1998) Circulation 97: 645-650. Lippincott Williams & Wilkins. U.S.A.

Shevde, et al., "Osteopontin knockdown suppresses tumorigenicity of human metastatic breast carcinoma, MDA-MB-435." Clin Exp Metastasis (2006) 23:123-133. Springer Science + Business Media B.V.

Sica, et al., "Edema mechanisms in the patient with heart failure and treatment options." (2008) Heart Failure Clin 4: 511-518. Elsevier Saunders.

Simons, et al., "Anti-sense c-myb oligonucleotides inhibit intimal arterial smooth muscle cell accumulation in vivo." (Sep. 3, 1992): Nature, 359:67-70. Nature Publishing Group.

Singh, et al., "Inhibition of connexin 43 synthesis-by antisense RNA in rat glioma cells." (1997) Cytobios 91:103-123. The Faculty Press. Great Britain.

Skolnick, et al., "Prom genes to protein structure and function: novel applications of computational approaches in the genomic era." (Jan. 2000) Tibtech 18:34-39. Elsevier Science, Ltd.

Smith, et al., "The challenges of genome sequence annotation or 'The devil is in the details'" (Nov. 1997) Nature Biotech 15:1222:1223.

Stein, et al., "Anti-sense o Igodeoxynucleotides-promises and pitfalls, (1992) Leukemia" 6:967-974. Office of the Journal of the Leukemia Society of America, Leukaemia Research Fund. United Kingdom.

Suzuki, et al., Protective effects of recombinant osteopontin on early brain injury after subarachnoid hemorrhage in rats. (2010) Crit Care Med 38(2):612-618.

Waggett, et al., Connexin 32 and 43 gap junctions differentially modulate tenocyte esonse to cyclic mechanical load. (2006) Eur. J. Cell. Bioi. 085:1145-1154. Elsevier GmbH.

Wagner, R. W. "Gene inhibition using anti-sense oligodeoxynucleotides" (1994) Nature, 372:333-335.

Wai, et al., "Osteopontin silencing by small interfering RNA suppresses in vitro and in vivo CT26 murine colon adenocarcinoma metastasis." (2005) Carcinogenesis 26(4):741-751. Oxford University Press.

Wells, et al., Additivity of mutational effects in proteins. (1990) Biochemistry 29 (37): 8509-8517.. American Chemical Society.

Willecke, et al., "Structural and functional diversity of connexin genes in the mouse and human genome." (May 2002) Biological Chemistry 383(5) 2002-05. Walter de Gruyter.

Willecke, et al., "Mouse connexin37: Cloning and functional expression of a gap function gene highly expressed in lung." (Sep. 1991) The Journal of Cell Biology 114(5):1049-1057. The Rockefeller University Press.

Wright, et al., "Connexin Mimetic Peptides Improve Cell Migration Rates of Human Epidermal Keratinocytes and Dermal Fibroblasts In Vitro." (2009) Wound Rep Reg 17:240-249. The Wound Healing Society.

Wright, et al., "Stage-Specific and Differential Expression of Gap Junctions in the Mouse Ovary: Connexin-Specific Roles in Follicular Regulation." (2001) J. Reprod. Fert. 121,77-88. Journals of Reproduction and Fertility.

Zhou, et al., "Blockade of Osteopontin Inhibits Glomerular Fibrosis in a Model of Anti-Glomerular Basement Membrane Glomerulonephritis." (Aug. 19, 2010) Am J Nephrol 32:324-331. Karger AG, Basel. (Published Online.).

Mori et al., "Molecular mechanisms linking wound inflammation and fibrosis: knockdown of osteopontin leads to rapid repair and reduced scarring," The Journal of Experimental Medicine, Jan. 21, 2008, 205(1):43-51 and online supplemental material, 13 total pages.

Notice of Final Rejection dated Mar. 27, 2014, from corresponding Japanese Patent Application No. 2010-539513, 4 total pages.

\* cited by examiner ial disorder that is characterized by
TREATMENT OF FIBROTIC CONDITIONS This application is a National Stage Application under 35 U.S.C. §371 of International Application No. PCT/US2008/014021, filed on Dec. 22, 2008 which claims the benefit of priority to U.S. Provisional Application No. 61/008,795 filed on Dec. 21, 2007. The disclosures of both are incorporated herein by reference.

FIELD

The inventions relate to connexins and gap junctions, and to fibrosis, fibrotic conditions, and methods of treatment thereof.

BACKGROUND

The following includes information that may be useful in understanding the present invention. It is not an admission that any of the information provided herein is prior art, or relevant, to the presently described or claimed inventions, or that any publication or document that is specifically or implicitly referenced is prior art.

In humans and other mammals wound injury triggers an organized complex cascade of cellular and biochemical events that will in most cases result in a healed wound. An ideally healed wound is one that restores normal anatomical structure, function, and appearance at the cellular, tissue, organ, and organism levels. Wound healing, whether initiated by surgery, disease, trauma, microbes or foreign materials, proceeds via a complex process encompassing a number of overlapping phases, including inflammation, epithelialization, angiogenesis and matrix deposition. Normally, these processes lead to a mature wound and a certain degree of scar formation.

Fibroproliferative diseases, including the pulmonary fibrosis, systemic sclerosis, liver cirrhosis, cardiovascular disease, progressive kidney disease, and macular degeneration, are a leading cause of morbidity and mortality and can affect all tissues and organ systems. Fibrotic tissue remodeling can also influence cancer metastasis and accelerate chronic graft rejection in transplant recipients. Nevertheless, despite its enormous impact on human health, there are currently no approved treatments that directly target the mechanism(s) of fibrosis.

Fibrosis is the abnormal accumulation of fibrous tissue that can occur as a part of the wound-healing process in damaged tissue. Examples of fibrosis include liver fibrosis, lung fibrosis (e.g., silicosis, asbestosis, idiopathic pulmonary fibrosis), oral fibrosis, endomyocardial fibrosis, retroperitoneal fibrosis, deltoid fibrosis, kidney fibrosis (including diabetic nephropathy), and glomerulosclerosis. Liver fibrosis, for example, occurs as a part of the wound-healing response to chronic liver injury. Fibrosis can occur as a complication of haemochromatosis, Wilson's disease, alcoholism, schistosomiasis, viral hepatitis, bile duct obstruction, exposure to toxins, and metabolic disorders. This formation of fibrotic tissue is believed to represent an attempt by the body to encapsulate injured tissue. Liver fibrosis is characterized by the accumulation of extracellular matrix that can be distinguished qualitatively from that in normal liver. Left unchecked, hepatic fibrosis progresses to cirrhosis (defined by the presence of encapsulated nodules), liver failure, and death. Endomyocardial fibrosis is an idiopathic disorder that is characterized by the development of restrictive cardiomyopathy. In endomyocardial fibrosis, the underlying process produces patchy fibrosis of the endocardial surface of the heart, leading to reduced compliance and, ultimately, restrictive physiology as the endomyocardial surface becomes more generally involved. Endocardial fibrosis principally involves the inflow tracts of the right and left ventricles and may affect the atrioventricular valves, leading to tricuspid and mitral regurgitation. Oral submucous fibrosis is a chronic, debilitating disease of the oral cavity characterized by inflammation and progressive fibrosis of the submucosal tissues (lamina propria and deeper connective tissues). It results in marked rigidity and an eventual inability to open the mouth. The buccal mucosa is the most commonly involved site, but any part of the oral cavity can be involved, even the pharynx. Retroperitoneal fibrosis is characterized by the development of extensive fibrosis throughout the retroperitoneum, typically centered over the anterior surface of the fourth and fifth lumbar vertebrae. This fibrosis leads to entrapment and obstruction of retroperitoneal structures, notably the ureters. In most cases, the etiology is unknown. However, its occasional association with autoimmune diseases and its response to corticosteroids and immunosuppressive therapy suggest it may be immunologically mediated. Deltoid fibrosis is a muscle disorder marked by intramuscular fibrous bands within the substance of the deltoid muscle. These bands lead to secondary contractures that affect the function of the shoulder joint. Scapular winging and secondary scoliosis also may be related to this condition. Deltoid fibrosis has been associated with fibrous contractures of the gluteal and quadriceps muscles and is likely a similar process Understanding of the cellular and biochemical mechanisms underlying liver fibrosis has advanced in recent years (reviewed by Li and Friedman, J. *Gastroenterol. Hepatol.* 14:618-633, 1999). Stellate cells are believed to be a major source of extracellular matrix in the liver. Stellate cells respond to a variety of cytokines present in the liver, some of which they also produce (Friedman, *Seminars in Liver Disease* 19:129-140, 1999). As summarized by Li and Friedman, actual and proposed therapeutic strategies for liver fibrosis include removal of the underlying cause (e.g., toxin or infectious agent), suppression of inflammation (using, e.g., corticosteroids, IL-1 receptor antagonists, or other agents that may suppress inflammation), down-regulation of stellate cell activation (using, e.g., gamma interferon or antioxidants), promotion of matrix degradation, or promotion of stellate cell apoptosis. Despite recent progress, many of these strategies are still in the experimental stage, and existing therapies are aimed at suppressing inflammation rather than addressing the underlying biochemical processes. Thus, there remains a need in the art for materials and methods for treating fibrosis, including liver fibrosis.

Gap junctions are cell membrane structures that facilitate direct cell-cell communication. A gap junction channel is formed of two connexons (hemichannels), each composed of six connexin subunits. Each hexameric connexon docks with a connexon in the opposing membrane to form a single gap junction. Gap junction channels are reported to be found throughout the body. Tissue such as the corneal epithelium, for example, has six to eight cell layers, yet is reported to expresses different gap junction channels in different layers with connexin 43 in the basal layer and connexin 26 from the basal to middle wing cell layers. In general, connexins are a family of proteins, commonly named according to their molecular weight or classified on a phylogenetic basis into alpha, beta, and gamma subclasses. At least 20 human and 19 murine isoforms have been identified. Different tissues and cell types are reported to have characteristic patterns of connexin protein expression and tissues such as cornea have been shown to alter connexin protein expression pattern following injury or transplantation (Qui, C. et al., (2003) *Current Biology,* 13:1967-1703; Brander et al., (2004), *J. Invest Dermatol.* 122:1310-20).

It has been reported that abnormal connexin function may be linked to certain disease states (e.g. heart diseases) (A. C. de Carvalho, et al., *J Cardiovasc Electrophysiol* 1994, 5 686). In certain connexin proteins, alterations in the turnover and trafficking properties may be induced by the addition exogenous agents which may affect the level of gap junctional intercellular communication (Darrow, B. J., et al. (1995). *Circ Res* 76: 381; Lin R, et al. (2001) *J Cell Biol* 154(4):815). Antisense technology has been reported for the modulation of the expression for genes implicated in viral, fungal and metabolic diseases. See, e.g., U.S. Pat. No. 5,166,195, (oligonucleotide inhibitors of HIV), U.S. Pat. No. 5,004,810 (oligomers for hybridizing to herpes simplex virus Vmw65 mRNA and inhibiting replication). See also U.S. Pat. No. 7,098,190 to Becker et al. (formulations comprising antisense nucleotides to connexins). Peptide inhibitors (including mimetic peptides) of gap junctions and hemichannels have been reported. See e.g. Berthoud, V. M. et al., *Am J. Physiol. Lung Cell Mol. Physiol.* 279:L619-L622 (2000); Evans, W. H. and Boitano, S. *Biochem. Soc. Trans.* 29: 606-612, and De Vriese A. S., et al. *Kidney Int.* 61:177-185 (2001). See also Becker and Green PCT/US06/04131 ("Anti-connexin compounds and uses thereof").

Despite advances in the understanding of the principles underlying fibrosis and the fibrotic process, there remains a significant unmet need in suitable therapeutic options for treatment of fibrosis and fibrotic conditions. Such therapeutics compositions and treatments are described and claimed herein.

BRIEF SUMMARY

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction.

According to one aspect, the present invention is directed to methods of decreasing fibrosis in a tissue of a subject comprising identifying a subject in need of decreased fibrosis and administering to the subject an anti-connexin polynucleotide, for example, an anti-connexin 43 polynucleotide, thereby decreasing fibrosis in the tissue of a subject. In certain embodiments, an anti-connexin polynucleotide is an anti-connexin 26, 30, 31.1, 32, 36, 37, 40, or 45 polynucleotide. In other embodiments, the anti-connexin polynucleotide is an anti-connexin 30.3, 31, 40.1, or 46.6 polynucleotide.

According to one embodiment the subject is a mammal. In another embodiment the mammal is a human. In another embodiment, the subject is an animal or a bird. Birds include pets and poultry. Animals include swine, cattle and sports animals and pets such as horses, dogs and cats.

According to one embodiment, the anti-connexin polynucleotide, e.g., anti-connexin 43 polynucleotide, decreases a target connexin, e.g., connexin 43, protein expression.

According to an embodiment, the anti-connexin polynucleotide, e.g., anti-connexin 43 polynucleotide, is an anti-connexin oligonucleotide, e.g., an anti-connexin 43, oligonucleotide.

According to an embodiment, the anti-connexin polynucleotide, e.g., anti-connexin 43 polynucleotide, is an antisense oligonucleotide, e.g., a connexin 43 antisense oligonucleotide.

According to an alternate embodiment, the anti-connexin polynucleotide, e.g., anti-connexin 43 polynucleotide, is an siRNA oligonucleotide. In another embodiment, the anti-connexin polynucleotide, e.g., anti-connexin 43 polynucleotide, is an RNAi oligonucleotide.

According to one embodiment of the present method, the tissue is skin tissue, retinal tissue, brain tissue, nerve tissue, lung tissue, cardiac tissue, kidney tissue or liver tissue. Other tissues where fibrosis occurs in the body are also within the scope of the invention.

According to another embodiment of the method, the anti-connexin polynucleotide, e.g., anti-connexin 43 polynucleotide, is administered to prevent or retard, in whole or in part, fibrosis.

According to one embodiment of the method, the subject has a disease, disorder or condition selected from the group consisting of scleroderma, kidney fibrosis (including diabetic nephropathy), cardiac fibrosis (e.g. myocardial fibrosis), pulomanry fibrosis (e.g., glomerulosclerosis pulmonary fibrosis, idiopathic pulmonary fibrosis, silicosis, asbestosis, interstitial lung disease and fibrotic lung disease, and chemotherapy/radiation induced pulmonary fibrosis), oral fibrosis, endomyocardial fibrosis, deltoid fibrosis, pancreatitis, inflammatory bowel disease, Crohn's disease, nodular fasciitis, eosinophilic fasciitis, general fibrosis syndrome characterized by replacement of normal muscle tissue by fibrous tissue in varying degrees, retroperitoneal fibrosis, liver fibrosis, liver cirrhosis, chronic renal failure; myelofibrosis (bone marrow fibrosis), drug induced ergotism, glioblastoma in Li-Fraumeni syndrome, sporadic glioblastoma, myleoid leukemia, acute myelogenous leukemia, myelodysplastic syndrome, myeloproferative syndrome, gynecological cancer, Kaposi's sarcoma, Hansen's disease, collagenous colitis and acute fibrosis. According to this embodiment, the scleroderma may be morphea, generalized morphea, or linear scleroderma. Also according to this embodiment, the kidney fibrosis may be glomerular sclerosis, renal tubulointerstitial fibrosis or progressive renal disease. Further to this embodiment, the pulmonary fibrosis may be diffuse interstitial pulmonary fibrosis.

According to another embodiment of the method, the fibrosis is acute fibrosis. The acute fibrosis may be in response to various forms of trauma including accidental injuries, infections, radiation or chemotherapy treatments.

According to another embodiment of the method, the fibrosis is chronic fibrosis.

The invention also includes methods for treating and/or preventing, in whole or in part, various diseases, disorders and conditions, including, for example, capsular contracture, Dupytren's contracture, Volkmann's contracture, Ledderhose's contracture, Peyronie's contracture or recurrence thereof, comprising administering a effective amount of a composition comprising an anti-connexin polynucleotide. In on embodiment, the composition is administered to the site of the injury before, at the time of and/or after a release procedure (e.g., forced manipulation, open release, arthroscopic release, or debulking of scar) to prevent the recurrence of scarred and abnormal tissue and/or further contracture.

According to a different embodiment, the connexin 43 is human connexin 43.

In an embodiment, the anti-connexin polynucleotide, e.g., anti-connexin 43 polynucleotide, inhibits intercellular communication by decreasing gap junction and/or hemichannel formation.

According to a further aspect, the patent invention is directed to a method of decreasing or preventing fibrosis in a subject in need thereof or at risk thereof, said method comprising administering a therapeutically effective amount, e.g., an anti-fibrotic amount, of an anti-connexin polynucleotide, e.g., anti-connexin 43 polynucleotide, to said subject. According to one embodiment of this aspect, the method comprises administering a therapeutically effective amount of an anti-connexin oligonucleotide to said subject. According to an alternate embodiment, the method comprises administering a therapeutically effective amount of an anti-connexin 43 oligonucleotide to said subject. In one embodiment, the anti-connexin polynucleotide is effective to downregulate connexin expression, preferably connexin 43 expression. In another embodiment, the anti-connexin polynucleotide or oligonucleotide is an antisense polynucleotide or oligonucleotide, e.g., an antisense connexin 43 polynucleotide or oligonucleotide. In yet another embodiment, the anti-connexin polynucleotide or oligonucleotide e.g., an anti-connexin 43 polynucleotide or oligonucleotide, or the antisense polynucleotide or oligonucleotide, e.g., an antisense connexin 43 polynucleotide or oligonucleotide, is an oligodeoxynucleotide.

According to the invention, polynucleotides, oligonucleotides, antisense polynucleotides, antisense oligonucleotides, oligodeoxynucleotides and antisense oligodeoxynucleotides may have unmodified or modified backbone structures.

According to one aspect, the anti-connexin polynucleotide, e.g., anti-connexin 43 polynucleotide, may be administered parenterally. Alternatively, according to this aspect, the anti-connexin polynucleotide, e.g., anti-connexin 43 polynucleotide, may be administered topically. Also, the anti-connexin polynucleotide, e.g., anti-connexin 43 polynucleotide, may be implanted or instilled or injected. The anti-connexin polynucleotide, e.g., anti-connexin 43 polynucleotide, may be administered in a sustained- or slow-release formulation.

Suitable anti-connexin 43 oligonucleotides may be selected from the group consisting of GTA ATT GCG GCA AGA AGA ATT GTT TCT GTC (SEQ. ID. NO:1); GTA ATT GCG GGA GGA ATT GTT TCT GTC (SEQ. ID. NO:2); and GGC AAG AGA CAC CAA AGA CAC TAC CAG CAT (SEQ. ID. NO:3).

According to an alternate aspect, the present invention is directed to a method to determine the anti-fibrotic activity of an anti-connexin polynucleotide, e.g., anti-connexin 43 polynucleotide, comprising contacting cells at risk of having or having fibrosis with an anti-connexin polynucleotide, e.g., anti-connexin 43 polynucleotide, and determining the anti-fibrotic effect of said anti-connexin polynucleotide, e.g., anti-connexin 43 polynucleotide. According to one embodiment, the method is carried out in vitro. According to an alternate embodiment, the method is carried out in vivo.

Compositions and formulations of the invention useful in treating or preventing fibrosis and fibrotic diseases, conditions and disorders that employ anti-connexin polynucleotides, including connexin antisense polynucleotides, are described and claimed.

In one aspect, the invention provides a pharmaceutical composition comprising one or more anti-connexin polynucleotides (e.g. connexin antisense polynucleotides). Preferably, the pharmaceutical composition further comprises a pharmaceutically acceptable carrier, diluent or excipient. For example, the inventions include pharmaceutical compositions comprising (a) a therapeutically effect amount of a pharmaceutically acceptable connexin antisense polynucleotide and (b) a pharmaceutically acceptable carrier or diluent.

The invention also includes pharmaceutical compositions useful in treating or preventing fibrosis and fibrotic diseases, disorders and conditions comprising (a) a therapeutically effective amount of an anti-connexin polynucleotide, and (b) a therapeutically effective amount of one or more therapeutic agents. The invention includes pharmaceutical compositions useful in treating or preventing fibrosis and fibrotic diseases, disorders and conditions comprising (a) a therapeutically effective amount of an anti-connexin polynucleotide, and (b) a therapeutically effective amount of one or more and/or agents useful in wound healing. The invention includes pharmaceutical compositions useful in treating or preventing fibrosis and fibrotic diseases, disorders and conditions comprising (a) a therapeutically effective amount of an anti-connexin polynucleotide, and (b) a therapeutically effective amount of one or more and/or anti-fibrotic agents. Preferably, the pharmaceutical compositions further comprise a pharmaceutically acceptable carrier, diluent or excipient.

Pharmaceutical compositions with one or more anti-connexin polynucleotides, alone or with one or more other anti-fibrotic agents, useful in treating or preventing fibrosis and fibrotic diseases, disorders and conditions are provided for combined, simultaneous, separate sequential or sustained administration. In one embodiment, a composition comprising one or more anti-connexin polynucleotides is administered at or about the same time as one or more therapeutic agents, and/or agents useful for wound healing and/or anti-fibrotic agents.

Examples of a connexin antisense polynucleotide include, for example, an anti-connexin oligodeoxynucleotide (ODN), including antisense (including modified and unmodified backbone antisense; e.g., a DNA antisense polynucleotide that binds to a connexin mRNA), RNAi, and siRNA polynucleotides.

Suitable connexin antisense polynucleotides include for example, antisense ODNs against connexin 43 (Cx43), connexin 26 (Cx26), connexin 37 (Cx37), connexin 30 (Cx30), connexin 31.1 (Cx31.1) and connexin 32 (Cx32). In certain embodiments, suitable compositions include multiple connexin antisense polynucleotides in combination, including for example, polynucleotides targeting Cx 43, 26, 30, and 31.1. Preferred connexin antisense polynucleotides target connexin 43.

Conveniently, the oligodeoxynucleotide to connexin 43 is selected from: GTA ATT GCG GCA AGA AGA ATT GTT TCT GTC (SEQ. ID. NO:1); GTA ATT GCG GCA GGA GGA ATT GTT TCT GTC (SEQ. ID. NO:2); GGC AAG AGA CAC CAA AGA CAC TAC CAG CAT (SEQ. ID. NO:3), a polynucleotide having at least about 70 percent homology with SEQ. ID. NOS:1, 2, or 3 or a polynucleotide which hybridizes to connexin 43 mRNA under conditions of medium to high stringency.

Pharmaceutical compositions useful in treating or preventing fibrosis and fibrotic diseases, disorders and conditions are also provided in the form of a combined preparation, for example, as an admixture of one or more anti-connexin polynucleotides and one or more other agents useful for wound healing, e.g., growth factors that are effective in promoting or improving wound healing, such as platelet derived growth factor, epidermal growth factor, fibroblast growth factor (e.g., FGF2), vascular endothelial growth factor, and transforming growth factor β3, and/or cytokines that are effective in promoting or improving wound healing, such as IL-7 and IL-10, and/or other agents that are effective in promoting or improving wound healing, such as IGF (e.g., IGF-1) and IGFBP (e.g., IGFBP-2).

The term "a combined preparation" includes a "kit of parts" in the sense that the combination partners as defined above can be dosed independently or by use of different fixed combinations with distinguished amounts of the combination partners (a) and (b), i.e. simultaneously, separately or sequentially. The parts of the kit can then, for example, be administered simultaneously or chronologically staggered, that is at different time points and with equal or different time intervals for any part of the kit of parts.

In a preferred embodiment, the administration of a combined preparation will have fewer administration time points and/or increased time intervals between administrations as a result of such combined use.

In another aspect, the invention includes methods for administering a therapeutically effective amount of one or more pharmaceutically acceptable connexin antisense polynucleotides formulated in a delayed release preparation, a slow release preparation, an extended release preparation, a controlled release preparation, and/or in a repeat action preparation to a subject with fibrosis or a fibrotic disease, disorder and condition.

In a further aspect, the invention includes transdermal patches, dressings, pads, wraps, matrices and bandages capable of being adhered or otherwise associated with the skin or other tissue of a subject, said articles being capable of delivering a therapeutically effective amount of one or more pharmaceutically acceptable anti-connexin polynucleotides, e.g., connexin antisense polynucleotides to a patient with fibrosis or fibrotic disease, disorder or condition.

The invention includes devices useful in treating or preventing fibrosis and fibrotic diseases, disorders and conditions containing therapeutically effective amounts of one or more pharmaceutically acceptable anti-connexin polynucleotides, e.g., connexin antisense polynucleotides, for example, a rate-controlling membrane enclosing a drug reservoir and a monolithic matrix device. These devices may be employed for the treatment of subjects in need thereof as disclosed herein. Suitably the dressing or matrix is provided including the form of a solid substrate with an anti-connexin polynucleotide, e.g., a connexin antisense polynucleotide, either alone or in combination with one or more therapeutic agents and/or agents useful for wound healing, dispersed on or in the solid substrate. In one embodiment the pharmaceutical product of the invention is provided in combination with a dressing or matrix. Preferred anti-connexin polynucleotides and connexin antisense polynucleotides are anti-connexin 43 polynucleotides and connexin 43 antisense polynucleotides.

In another aspect, the invention includes an article of manufacture useful in treating or preventing fibrosis and fibrotic diseases, disorders and conditions comprising a vessel containing a therapeutically effective amount of one or more pharmaceutically acceptable anti-connexin polynucleotides, e.g., connexin antisense polynucleotides, and instructions for use. Such instructions may include instructions regarding use for the treatment of a subject having a fibrosis or a fibrotic disease, disorder or condition. Preferred anti-connexin polynucleotides and connexin antisense polynucleotides are anti-connexin 43 polynucleotides and connexin 43 antisense polynucleotides. In one embodiment, the vessel further comprises a therapeutically effective amount of one or more therapeutic agents and/or agents useful for wound healing. In one embodiment, the article of manufacture additionally comprises a vessel containing a therapeutically effective amount of one or more therapeutic agents and/or agents useful for wound healing.

The invention includes an article of manufacture useful in treating or preventing fibrosis and fibrotic diseases, disorders and conditions comprising packaging material containing one or more dosage forms containing one or more pharmaceutically acceptable anti-connexin polynucleotides, e.g., connexin antisense polynucleotides, wherein the packaging material has a label that indicates that the dosage form can be used for a subject having or suspected of having or predisposed to any of the diseases, disorders and/or conditions described or referenced herein, including fibrosis or a fibrotic disease, disorder or condition. Such dosage forms include, for example, topical delivery forms and formulations. Preferred anti-connexin polynucleotides and connexin antisense polynucleotides are anti-connexin 43 polynucleotides and connexin 43 antisense polynucleotides. In one embodiment, the dosage form further comprises a therapeutically effective amount of one or more therapeutic agents and/or agents useful for wound healing. In one embodiment, the dosage form additionally comprises a vessel containing a therapeutically effective amount of one or more therapeutic agents and/or agents useful for wound healing.

DETAILED DESCRIPTION

Definitions

As used herein, a "disorder" is any disorder, disease, or condition that would benefit from an agent that reduces or retards fibrosis. For example, included are diseases, disorders and conditions characterized by excess production of fibrous material, including excess production of fibrous material within the extracellular matrix. Also included are diseases, disorders and conditions characterized by replacement of normal tissue elements by abnormal, non-functional, and/or excessive accumulation of matrix-associated components.

As used herein, "subject" refers to any mammal, including humans, domestic and farm animals, and zoo, sports, and pet animals, such as dogs, horses, cats, sheep, pigs, cows, etc. The preferred mammal herein is a human, including adults, children, and the elderly. A subject may also be a bird, including zoo, sports, and pet birds.

As used herein, "preventing" means preventing in whole or in part, or ameliorating or controlling, or reducing, retarding or halting the production or occurrence of the thing or event to be prevented.

As used herein, a "therapeutically effective amount" or "effective amount" in reference to the compounds or compositions of the instant invention refers to the amount sufficient to induce a desired biological, pharmaceutical, or therapeutic result. That result can be alleviation of the signs, symptoms, or causes of a disease or disorder or condition, or any other desired alteration of a biological system. In the present invention, the result will involve preventing fibrosis.

As used herein, the term "treating" refers to both therapeutic treatment and prophylactic or preventative measures. Those in need of treatment include those already with the disorder as well as those prone to having the disorder or diagnosed with the disorder or those in which the disorder is to be prevented. Thus, anti-fibrotic applications of compounds and compositions and formulations of the invention administered prior to the formation of fibrosis or fibrotic tissue are within the invention.

As used herein, "simultaneously" is used to mean that the one or more anti-connexin polynucleotides, alone or in combination with one or more therapeutic agents and/or agents useful for wound healing are administered concurrently, whereas the term "in combination" is used to mean the polynucleotides and/or agents are administered, if not simultaneously or in physical combination, then "sequentially" within a timeframe that they both are available to act therapeutically. Thus, administration "sequentially" may permit one polynucleotide or agent to be administered within minutes (for example, 1, 2, 3, 4, 5, 10, 15, 20, 25, 30) minutes or a matter of hours, days, weeks or months after the other polynucleotide or agent provided that both are concurrently present in therapeutically effective amounts. The time delay between administration of the components will vary depending on the exact nature of the components, the interaction there between, and their respective half-lives.

As used herein, an "anti-connexin polynucleotide" decreases or inhibits expression of connexin mRNA and/or protein. Anti-connexin polynucleotides include, without limitation, antisense compounds such as antisense polynucleotides, other polynucleotides (such as polynucleotides having siRNA or ribozyme functions). Suitable examples of an anti-connexin polynucleotide include an antisense polynucleotide to a connexin. Accordingly, suitable anti-connexin polynucleotides include, for example, antisense polynucleotides (e.g., connexin 43 antisense polynucleotides) that modulate expression or activity of connexins and gap junctions in selected tissues, cells, and subjects. Exemplary anti-connexin polynucleotides are further described herein.

As used herein, "fibrotic" diseases, disorders, or conditions include those mentioned herein, and further include acute and chronic, clinical or sub-clinical presentation, in which fibrogenic associated biology or pathology is evident. Fibrotic diseases, disorders, or conditions include diseases, disorders or conditions characterized, in whole or in part, by the excess production of fibrous material, including excess production of fibrotic material within the extracellular matrix, or the replacement of normal tissue elements by abnormal, non-functional, and/or excessive accumulation of matrix-associated components. Fibrotic diseases, disorders, or conditions include, for example, fibrogenic-related biology or pathology characterized by fibrosis.

Exemplary fibrotic diseases, disorders and conditions include, for example, scleroderma (including morphea, generalized morphea, or linear scleroderma), kidney fibrosis (including glomerular sclerosis, renal tubulointerstitial fibrosis, progressive renal disease or diabetic nephropathy), cardiac fibrosis (e.g. myocardial fibrosis), pulomanry fibrosis (e.g., glomerulosclerosis pulmonary fibrosis, idiopathic pulmonary fibrosis, silicosis, asbestosis, interstitial lung disease, interstitial fibrotic lung disease, and chemotherapy/radiation induced pulmonary fibrosis), oral fibrosis, endomyocardial fibrosis, deltoid fibrosis, pancreatitis, inflammatory bowel disease, Crohn's disease, nodular fascilitis, eosinophilic fasciitis, general fibrosis syndrome characterized by replacement of normal muscle tissue by fibrous tissue in varying degrees, retroperitoneal fibrosis, liver fibrosis, liver cirrhosis, chronic renal failure; myelofibrosis (bone marrow fibrosis), drug induced ergotism, glioblastoma in Li-Fraumeni syndrome, sporadic glioblastoma, myleoid leukemia, acute myelogenous leukemia, myelodysplastic syndrome, myeloproferative syndrome, gynecological cancer, Kaposi's sarcoma, Hansen's disease, collagenous colitis and acute fibrosis.

Fibrotic diseases, disorders and conditions may also include contractures. Contractures, including post-operative contractures, refer to a permanent or long term reduction of range of motion due to tonic spasm or fibrosis, or to loss of normal tissue compliance, motion or equilibrium (e.g., muscle, tendon, ligament, fascia, synovium, joint capsule, other connective tissue, or fat). In general, the condition of contracture may involve a fibrotic response with inflammatory components, both acute and chronic. Some of which may be associated with surgery, including a release procedure. Hereditary contractures such as Dupytren's contracture, Peyronie's disease, and Ledderhose's disease are also included.

Fibrosis can be either chronic or acute. Fibrotic conditions include excessive amounts of fibrous tissue, including excessive amounts of extracellular matrix accumulation within a tissue, forming tissue which causes dysfunction and, potentially, organ failure. Chronic fibrosis includes fibrosis of the major organs, most commonly lung, liver, kidney and/or heart. Acute fibrosis (usually with a sudden and severe onset and of short duration) occurs typically as a common response to various fauns of trauma including injuries, ischemic illness (e.g. cardiac scarring following heart attack), environmental pollutants, alcohol and other types of toxins, acute respiratory distress syndrome, radiation and chemotherapy treatments. All tissues damaged by trauma can become fibrotic, particularly if the damage is repeated.

Response to injury has been reported to involve coordinated and temporally regulated patterns of mediators and sequence of cellular events in tissues subsequent to injury. The initial injury is reported to trigger coagulation cascade and an acute local inflammatory response followed by mesenchymal cell recruitment, proliferation and matrix synthesis. Uncontrolled matrix accumulation, often involving aberrant cytokine pathways, can lead to fibrotic conditions or disorders. Progressive fibrosis in vital organs such as the lung, kidney, liver, heart, brain and bone marrow, is both a major cause of illness and death.

Anti-Connexin Polynucleotides

Anti-connexin polynucleotides include connexin antisense polynucleotides as well as polynucleotides which have functionalities that enable them to downregulate or otherwise inhibit connexin expression (for example, by downregulation or inhibition of mRNA transcription or translation). In the case of downregulation, this will have the effect of reducing direct cell-cell communication by gap junctions, or access to the extracellular space through hemichannels, at the site at which connexin expression is down-regulated.

Suitable anti-connexin polynucleotides include antisense oligonucleotides (including antisense oligodeoxynucleotides), RNAi polynucleotides and siRNA polynucleotides.

Synthesis of antisense polynucleotides and other anti-connexin polynucleotides such as RNAi, siRNA, and ribozyme polynucleotides as well as polynucleotides having modified and mixed backbones is known to those of skill in the art. See e.g. Stein C. A. and Krieg A. M. (eds), Applied Antisense Oligonucleotide Technology, 1998 (Wiley-Liss).

According to one aspect, the downregulation of connexin expression may be based generally upon the antisense approach using antisense polynucleotides (such as DNA or RNA polynucleotides), and more particularly upon the use of antisense oligodeoxynucleotides (ODN). These polynucleotides (e.g., ODN) target the connexin protein(s) to be down-regulated. Typically the polynucleotides are single stranded, but may be double stranded.

The antisense polynucleotide may inhibit transcription and/or translation of a connexin. Preferably the polynucleotide is a specific inhibitor of transcription and/or translation from the connexin gene or mRNA, and does not inhibit transcription and/or translation from other genes or mRNAs. The product may bind to the connexin gene or mRNA either (i) 5' to the coding sequence, and/or (ii) to the coding sequence, and/or (iii) 3' to the coding sequence.

The antisense polynucleotide is generally antisense to a connexin mRNA. Such a polynucleotide may be capable of hybridizing to the connexin mRNA and may thus inhibit the expression of connexin by interfering with one or more aspects of connexin mRNA metabolism including transcription, mRNA processing, mRNA transport from the nucleus, translation or mRNA degradation. The antisense polynucleotide typically hybridizes to the connexin mRNA to form a duplex which can cause direct inhibition of translation and/or destabilization of the mRNA. Such a duplex may be susceptible to degradation by nucleases.

The antisense polynucleotide may hybridize to all or part of the connexin mRNA. Typically the antisense polynucleotide hybridizes to the ribosome binding region or the coding region of the connexin mRNA. The polynucleotide may be complementary to all of or a region of the connexin mRNA. For example, the polynucleotide may be the exact complement of all or a part of connexin mRNA. However, absolute complementarity is not required and polynucleotides which have sufficient complementarity to form a duplex having a melting temperature of greater than about 20° C., 30° C. or 40° C. under physiological conditions are particularly suitable for use in the present invention.

Thus the polynucleotide is typically a homologue of a sequence complementary to the mRNA. The polynucleotide may be a polynucleotide which hybridizes to the connexin mRNA under conditions of medium to high stringency such as 0.03M sodium chloride and 0.03M sodium citrate at from about 50° C. to about 60° C.

For certain aspects, suitable polynucleotides are typically from about 6 to 40 nucleotides in length. Preferably a polynucleotide may be from about 12 to about 35 nucleotides in length, or alternatively from about 12 to about 20 nucleotides in length or more preferably from about 18 to about 32 nucleotides in length. According to an alternative aspect, the polynucleotide may be at least about 40, for example at least about 60 or at least about 80, nucleotides in length and up to about 100, about 200, about 300, about 400, about 500, about 1000, about 2000 or about 3000 or more nucleotides in length.

The connexin protein or proteins targeted by the polynucleotide will be dependent upon the site at which downregulation is to be effected. This reflects the non-uniform make-up of gap junction(s) at different sites throughout the body in terms of connexin sub-unit composition. The connexin is a connexin that naturally occurs in a human or animal in one aspect or naturally occurs in the tissue in which connexin expression or activity is to be decreased. The connexin gene (including coding sequence) generally has homology with the coding sequence of one or more of the specific connexins mentioned herein, such as homology with the connexin 43 coding sequence shown in Table 2. The connexin is typically an α or β connexin. Preferably the connexin is an α connexin and is expressed in the tissue to be treated.

Some connexin proteins are however more ubiquitous than others in terms of distribution in tissue. One of the most widespread is connexin 43. Polynucleotides targeted to connexin 43 are particularly suitable for use in the present invention. In other aspects other connexins are targeted.

In one preferred aspect, the antisense polynucleotides are targeted to the mRNA of one connexin protein only. Most preferably, this connexin protein is connexin 43. In another aspect, connexin protein is connexin 26, 30, 31.1, 32, 36, 37, 40, or 45. In other aspects, the connexin protein is connexin 30.3, 31, 40.1, or 46.6.

It is also contemplated that polynucleotides targeted to separate connexin proteins be used in combination (for example 1, 2, 3, 4 or more different connexins may be targeted). For example, polynucleotides targeted to connexin 43, and one or more other members of the connexin family (such as connexin 26, 30, 30.3, 31.1, 32, 36, 37, 40, 40.1, 45, and 46.6) can be used in combination.

Alternatively, the antisense polynucleotides may be part of compositions which may comprise polynucleotides to more than one connexin protein. Preferably, one of the connexin proteins to which polynucleotides are directed is connexin 43. Other connexin proteins to which oligodeoxynucleotides are directed may include, for example, connexins 26, 30, 30.3, 31.1, 32, 36, 37, 40, 40.1, 45, and 46.6. Suitable exemplary polynucleotides (and ODNs) directed to various connexins are set forth in Table 1.

Individual antisense polynucleotides may be specific to a particular connexin, or may target 1, 2, 3 or more different connexins. Specific polynucleotides will generally target sequences in the connexin gene or mRNA which are not conserved between connexins, whereas non-specific polynucleotides will target conserved sequences for various connexins.

The polynucleotides for use in the invention may suitably be unmodified phosphodiester oligomers. Such oligodeoxynucleotides may vary in length. A 30 mer polynucleotide has been found to be particularly suitable.

Many aspects of the invention are described with reference to oligodeoxynucleotides. However it is understood that other suitable polynucleotides (such as RNA polynucleotides) may be used in these aspects.

The antisense polynucleotides may be chemically modified. This may enhance their resistance to nucleases and may enhance their ability to enter cells. For example, phosphorothioate oligonucleotides may be used. Other deoxynucleotide analogs include methylphosphonates, phosphoramidates, phosphorodithioates, N3'P5'-phosphoramidates and oligoribonucleotide phosphorothioates and their 2'-O-alkyl analogs and 2'-O-methylribonucleotide methylphosphonates. Alternatively mixed backbone oligonucleotides ("MBOs") may be used. MBOs contain segments of phosphothioate oligodeoxynucleotides and appropriately placed segments of modified oligodeoxy- or oligoribonucleotides. MBOs have segments of phosphorothioate linkages and other segments of other modified oligonucleotides, such as methylphosphonate, which is non-ionic, and very resistant to nucleases or 2'-O-alkyloligoribonucleotides. Methods of preparing modified backbone and mixed backbone oligonucleotides are known in the art.

The precise sequence of the antisense polynucleotide used in the invention will depend upon the target connexin protein. In one embodiment, suitable connexin antisense polynucleotides can include polynucleotides such as oligodeoxynucleotides selected from the following sequences set forth in Table 1:

TABLE 1

| | | |
|---|---|---|
| 5' GTA ATT GCG GCA AGA AGA ATT GTT TCT GTC 3' | (connexin 43) | (SEQ. ID. NO: 1) |
| 5' GTA ATT GCG GCA GGA GGA ATT GTT TCT GTC 3' | (connexin 43) | (SEQ. ID. NO: 2) |
| 5' GGC AAG AGA CAC CAA AGA CAC TAC CAG CAT 3' | (connexin 43) | (SEQ. ID. NO: 3) |
| 5' TCC TGA GCA ATA CCT AAC GAA CAA ATA 3' | (connexin 26) | (SEQ. ID. NO: 4) |
| 5' CAT CTC CTT GGT GCT CAA CC 3' | (connexin 37) | (SEQ. ID. NO: 5) |

TABLE 1-continued

| | |
|---|---|
| 5' CTG AAG TCG ACT TGG CTT GG 3' (connexin 37) | (SEQ. ID. NO: 6) |
| 5' CTC AGA TAG TGG CCA GAA TGC 3' (connexin 30) | (SEQ. ID. NO: 7) |
| 5' TTG TCC AGG TGA CTC CAA GG 3' (connexin 30) | (SEQ. ID. NO: 8) |
| 5' CGT CCG AGC CCA GAA AGA TGA GGT C 3' (connexin 31.1) | (SEQ. ID. NO: 9) |
| 5' AGA GGC GCA CGT GAG ACA C 3' (connexin 31.1) | (SEQ. ID. NO: 10) |
| 5' TGA AGA CAA TGA AGA TGT T 3' (connexin 31.1) | (SEQ. ID. NO: 11) |
| 5' TTT CTT TTC TAT GTG CTG TTG GTG A 3' (connexin 32) | (SEQ. ID. NO: 12) |

Suitable polynucleotides for the preparation of the combined polynucleotide compositions described herein include for example, polynucleotides to connexin 43 and polynucleotides for connexins 26, 30, 31.1, 32 and 37 as described in Table 1 above.

Although the precise sequence of the antisense polynucleotide used in the invention will depend upon the target connexin protein, for connexin 43, antisense polynucleotides having the following sequences have been found to be particularly suitable:

```
                                    (SEQ. ID. NO: 1)
    GTA ATT GCG GCA AGA AGA ATT GTT TCT GTC;

(SEQ. ID. NO: 2)
    GTA ATT GCG GCA GGA GGA ATT GTT TCT GTC;
    and (SEQ. ID. NO: 3)
    GGC AAG AGA CAC CAA AGA CAC TAC CAG CAT.
```

For example, suitable antisense polynucleotides for connexins 26, 31.1 and 32 have the following sequences:

```
                                    (SEQ. ID. NO: 4)
    5' TCC TGA GCA ATA CCT AAC GAA CAA ATA
    (connexin 26);

(SEQ. ID. NO: 9)
    5' CGT CCG AGC CCA GAA AGA TGA GGT C
    (connexin 31.1); and (SEQ. ID. NO: 12)
    5' TTT CTT TTC TAT GTG CTG TTG GTG A
    (connexin 32).
```

Other connexin antisense polynucleotide sequences useful according to the methods of the present invention include:

```
                                    (SEQ. ID. NO: 5)
    5' CAT CTC CTT GGT GCT CAA CC 3' (connexin 37);

(SEQ. ID. NO: 6)
    5' CTG AAG TCG ACT TGG CTT GG 3' (connexin 37);

(SEQ. ID. NO: 7)
    5' CTC AGA TAG TGG CCA GAA TGC 3' (connexin 30);

(SEQ. ID. NO: 8)
    5' TTG TCC AGG TGA CTC CAA GG 3' (connexin 30);

(SEQ. ID. NO: 10)
    5' AGA GGC GCA CGT GAG ACA C 3' (connexin 31.1);
    and (SEQ. ID. NO: 11)
    5' TGA AGA CAA TGA AGA TGT T 3' (connexin 31.1).
```

Polynucleotides, including ODN's, directed to connexin proteins can be selected in terms of their nucleotide sequence by any convenient, and conventional, approach. For example, the computer programs MacVector and OligoTech (from Oligos etc. Eugene, Oreg., USA) can be used. Once selected, the ODN's can be synthesized using a DNA synthesizer.

Polynucleotide Homologues

Anti-connexin polynucleotides also include polynucleotide homologues. Homology and homologues are discussed herein (for example, the polynucleotide may be a homologue of a complement to a sequence in connexin mRNA). Such a polynucleotide typically has at least about 70% homology, preferably at least about 80%, at least about 90%, at least about 95%, at least about 97% or at least about 99% homology with the relevant sequence, for example over a region of at least about 15, at least about 20, at least about 40, at least about 100 more contiguous nucleotides (of the homologous sequence).

Homology may be calculated based on any method in the art. For example the UWGCG Package provides the BESTFIT program, which can be used to calculate homology (for example used on its default settings) (Devereux et al. (1984) *Nucleic Acids Research* 12, p 387-395). The PILEUP and BLAST algorithms can be used to calculate homology or line up sequences (typically on their default settings), for example as described in Altschul S. F. (1993) *J Mol Evol* 36: 290-300; Altschul, S, F et al (1990) *J Mol Biol* 215: 403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached.

The BLAST algorithm parameters W, T and X determine the sensitivity and speed of the alignment. The BLAST program uses as defaults a word length (W), the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to a second sequence is less than about 1, preferably less than about 0.1, more preferably less than about 0.01, and most preferably less than about 0.001.

The homologous sequence typically differs from the relevant sequence by at least about (or by no more than about) 2, 5, 10, 15, 20 more mutations (which may be substitutions, deletions or insertions). These mutations may be measured across any of the regions mentioned above in relation to calculating homology.

The homologous sequence typically hybridizes selectively to the original sequence at a level significantly above background. Selective hybridization is typically achieved using conditions of medium to high stringency (for example 0.03M sodium chloride and 0.03M sodium citrate at from about 50° C. to about 60° C.). However, such hybridization may be carried out under any suitable conditions known in the art (see Sambrook et al. (1989), Molecular Cloning: A Laboratory Manual). For example, if high stringency is required, suitable conditions include 0.2×SSC at 60° C. If lower stringency is required, suitable conditions include 2×SSC at 60° C.

Therapeutic Agents

Therapeutic agents include pharmaceutically acceptable agents useful in the treatment of wounds or the promotion of wound-healing, whether currently existing and known or later developed. Therapeutic agents include, for example, anti-infectives, anesthetics, analgesics, antibiotics, narcotics, and steroidal and non-steroidal anti-inflammatory agents. Preferred therapeutic agents include topical steroid anti-inflammatory agents, antimicrobial agents, local and topical anesthetics, and topical opioids. In certain embodiments, one, two three, four, five or six therapeutic agents may be used in combination. In other embodiments, the therapeutic agent is not an anti-connexin peptide, e.g., an anti-connexin peptidomimetic.

Agents Useful for Wound Healing

As used herein, agents useful for wound healing include stimulators, enhancers or positive mediators of the wound healing cascade which 1) promote or accelerate the natural wound healing process or 2) reduce effects associated with improper or delayed wound healing, which effects include, for example, adverse inflammation, epithelialization, angiogenesis and matrix deposition, and scarring and fibrosis. In certain embodiments, the therapeutic agent is not an anti-connexin peptide, e.g., an anti-connexin peptidomimetic.

Positive mediators, enhancers and stimulators include for example, an agent which may stimulate, enhance, facilitate, or accelerate (i.e., agonize) the quantity, quality or efficacy of wound healing or the active wound healing process, or a wound healing-associated growth factor or cytokine at a wound site, or the activation of a wound healing-associated growth factor or cytokine receptor. Such agents may include a wound healing-associated growth factor or cytokine or a partially modified form of a wound healing-associated growth factor or cytokine, for example. A partially modified form of wound healing-associated growth factor or cytokine may, for example, have a longer half-life than the natural wound healing-associated growth factor or cytokine. Alternatively, it may be an inhibitor of wound healing-associated growth factor or cytokine metabolism.

Agents useful for wound healing also include anti-fibrotic agents, which include, for example, any agent which can prevent and/or suppress, reduce or improve fibrogenic pathology. Exemplary anti-fibrotic agents include, for example, direct or indirect regulators associated with the wound-associated inflammatory reaction, recruitment of neutrophils to the site of injury; activation and recruitment of macrophages and endothelial cells; recruitment and activation of lymphocytes and/or eosinophils via secretion of a number of cytokines/chemokines; release of cytotoxic mediators and fibrogenic cytokines; recruiting and activating cell proliferation, ECM synthesis and angiogenesis.

Partial modification of such an agent may be by way of addition, deletion or substitution of amino acid residues. A substitution may for example be a conserved substitution. Hence a partially modified molecule may be a homologue of the molecule from which it was derived. It may have at least about 40%, for example about 50, 60, 70, 80, 90 or 95%, homology with the molecule from which it is derived.

As used herein, agents useful for wound healing may include for example, wound-healing-promoting or scar-reducing agents for wound treatment modalities now known in the art or later-developed; exemplary factors, agents or modalities including natural or synthetic growth factors, cytokines, or modulators thereof to promote wound healing, wound healing promoting bioengineered matrix, dressings bandages, and the like. Suitable examples may include, but not limited to 1) topical or dressing and related therapies and debriding agents (such as, for example, Santyl® collagenase) and Iodosorb® (cadexomer iodine); 2) antimicrobial agents, including systemic or topical creams or gels, including, for example, silver-containing agents such as SAGs (silver antimicrobial gels), (CollaGUARD™, Innocoll, Inc) (purified type-I collagen protein based dressing), CollaGUARD Ag (a collagen-based bioactive dressing impregnated with silver for infected wounds or wounds at risk of infection), DermaSIL™ (a collagen-synthetic foam composite dressing for deep and heavily exuding wounds); 3) cell therapy or bioengineered skin, skin substitutes, and skin equivalents, including, for example, Dermograft (3-dimensional matrix cultivation of human fibroblasts that secrete cytokines and growth factors), Apligraf® (human keratinocytes and fibroblasts), Graftskin® (bilayer of epidermal cells and fibroblasts that is histologically similar to normal skin and produces growth factors similar to those produced by normal skin), TransCyte (a Human Fibroblast Derived Temporary Skin Substitute) and Oasis® (an active biomaterial that comprises both growth factors and extracellular matrix components such as collagen, proteoglycans, and glycosaminoglycans); 4) cytokines, growth factors or hormones (both natural and synthetic) introduced to the wound to promote wound healing, including, for example, NGF, NT3, BDGF, integrins, plasmin, semaphoring, blood-derived growth factor, keratinocyte growth factor, tissue growth factor, TGF-alpha, TGF-beta, PDGF (one or more of the three subtypes may be used: AA, AB, and B), PDGF-BB, TGF-beta 3, factors that modulate the relative levels of TGFβ3, TGFβ1, and TGFβ2 (e.g., Mannose-6-phosphate), sex steroids, including for example, estrogen, estradiol, or an oestrogen receptor agonist selected from the group consisting of ethinyloestradiol, dienoestrol, mestranol, oestradiol, oestriol, a conjugated oestrogen, piperazine oestrone sulphate, stilboestrol, fosfesterol tetrasodium, polyestradiol phosphate, tibolone, a phytoestrogen, 17-beta-estradiol; thymic hormones such as Thymosin-beta-4, EGF, HB-EGF, fibroblast growth factors (e.g., FGF1, FGF2, FGF7), keratinocyte growth factor, TNF, interleukins family of inflammatory response modulators such as, for example, IL-10, IL-1, IL -2, IL-6, IL-8, and IL-10 and modulators thereof; INFs (INF-alpha, -beta, and -delta); stimulators of activin or inhibin, and inhibitors of interferon gamma prostaglandin E2 (PGE2) and of mediators of the adenosine 3',5'-cyclic monophosphate (cAMP) pathway; adenosine A1 agonist, adenosine A2 agonist or 5) other agents useful for wound healing, including, for example, both natural or synthetic homologues, agonist and antagonist of VEGF, VEGFA, IGF; IGF-1, proinflammatory cytokines, GM-CSF, and leptins and 6) IGF-1 and KGF cDNA, autologous platelet gel, hypochlorous acid (Sterilox®) lipoic acid, nitric oxide synthase3, matrix metalloproteinase 9 (MMP-9), CCT-ETA, alphavbeta6 integrin, growth factor-primed fibroblasts and Decorin, silver containing wound dressings, Xenaderm™, papain wound debriding agents, lactoferrin, substance P, collagen, and silver-ORC, placental alkaline phosphatase or placental growth factor, modulators of hedgehog signaling, modulators of cholesterol synthesis pathway, and APC (Activated Protein C), keratinocyte growth factor, TNF, Thromboxane A2, NGF, BMP bone morphogenetic protein, CTGF (connective tissue growth factor), wound healing chemokines, decorin, modulators of lactate induced neovascularization, cod liver oil, placental alkaline phosphatase or placental growth factor, and thymosin beta 4. In certain embodiments, one, two three, four, five or six agents useful for wound healing may be used in combination.

It is to be understood that the agents useful for wound healing (including for example, growth factors and cytokines) above encompass all naturally occurring polymorphs (for example, polymorphs of the growth factors or cytokines). Also, functional fragments, chimeric proteins comprising one of said agents useful for wound healing or a functional fragment thereof, homologues obtained by analogous substitution of one or more amino acids of the agent useful for wound healing, and species homologues are encompassed. It is contemplated that one or more agents useful for wound healing may be a product of recombinant DNA technology, and one or more agents useful for wound healing may be a product of transgenic technology. For example, platelet derived growth factor may be provided in the form of a recombinant PDGF or a gene therapy vector comprising a coding sequence for PDGF.

A fragment or partially modified form thereof refers to a fragment or partially modified form of the agent useful for wound healing which retains the biological or wound healing functionality of the factor, although it may of course have additional functionality. Partial modification may, for example, be by way of addition, deletion or substitution of amino acid residues. For example, a substitution may be a conserved substitution. Hence the partially modified molecules may be homologues of the agent useful for wound healing. They may, for example, have at least about 40% homology with said factor. They may for example have at least about 50, 60, 70, 80, 90 or 95% homology with said factor. For example, in certain embodiments, IL-10 or a fragment or a partially modified form thereof may be administered at a concentration of between about 1 µM and about 10 µM. It may be administered at a concentration of between about 2.5 µM and about 5 µM. In certain other embodiments, IL-10 or a fragment or a partially modified form thereof may be administered immediately prior to wound healing, but may be effective if administered within about 7 days of wounding. It could be administered on at least two occasions.

Dosage Forms and Formulations and Administration

The agents of the invention of the may be administered to a subject in need of treatment, such as a subject with, or at risk for, any of the diseases, disorders or conditions mentioned herein. The condition of the subject can thus be improved. The anti-connexin polynucleotide may be used in the treatment of the subject's body by therapy. They may be used in the manufacture of a medicament to treat any of the diseases, disorders or conditions mentioned herein.

The anti-connexin polynucleotide may be present in a substantially isolated form. It will be understood that the product may be mixed with carriers or diluents which will not interfere with the intended purpose of the product and still be regarded as substantially isolated. A product of the invention may also be in a substantially purified form, in which case it will generally comprise about 80%, 85%, or 90%, including, for example, at least about 95%, at least about 98% or at least about 99% of the polynucleotide or dry mass of the preparation.

Depending on the intended route of administration, the pharmaceutical products, pharmaceutical compositions, combined preparations and medicaments of the invention may, for example, take the form of solutions, suspensions, instillations, sprays, salves, creams, gels, foams, ointments, emulsions, lotions, paints, sustained release formulations, or powders, and typically contain about 0.01% to about 1% of active ingredient(s), about 1%-50% or active ingredient(s), about 2%-60% of active ingredient(s), about 2%-70% of active ingredient(s), or up to about 90% of active ingredient(s). Other suitable formulations include pluronic gel-based formulations, carboxymethylcellulose (CMC)-based formulations, and hyroxypropylmethylcellulose (HPMC)-based formulations. Other useful formulations include slow or delayed release preparations.

Gels or jellies may be produced using a suitable gelling agent including, but not limited to, gelatin, tragacanth, or a cellulose derivative and may include glycerol as a humectant, emollient, and preservative. Ointments are semi-solid preparations that consist of the active ingredient incorporated into a fatty, waxy, or synthetic base. Examples of suitable creams include, but are not limited to, water-in-oil and oil-in-water emulsions. Water-in-oil creams may be formulated by using a suitable emulsifying agent with properties similar, but not limited, to those of the fatty alcohols such as cetyl alcohol or cetostearyl alcohol and to emulsifying wax. Oil-in-water creams may be formulated using an emulsifying agent such as cetomacrogol emulsifying wax. Suitable properties include the ability to modify the viscosity of the emulsion and both physical and chemical stability over a wide range of pH. The water soluble or miscible cream base may contain a preservative system and may also be buffered to maintain an acceptable physiological pH.

Foam preparations may be formulated to be delivered from a pressurized aerosol canister, via a suitable applicator, using inert propellants. Suitable excipients for the formulation of the foam base include, but are not limited to, propylene glycol, emulsifying wax, cetyl alcohol, and glyceryl stearate. Potential preservatives include methylparaben and propylparaben.

Preferably the agents of the invention are combined with a pharmaceutically acceptable carrier or diluent to produce a pharmaceutical composition. Suitable carriers and diluents include isotonic saline solutions, for example phosphate-buffered saline. Suitable diluents and excipients also include, for example, water, saline, dextrose, glycerol, or the like, and combinations thereof. In addition, if desired substances such as wetting or emulsifying agents, stabilizing or ph buffering agents may also be present.

The term "pharmaceutically acceptable carrier" refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, and amino acid copolymers.

Pharmaceutically acceptable salts can also be present, e.g., mineral acid salts such as hydrochlorides, hydrobromides, phosphates, sulfates, and the like; and the salts of organic acids such as acetates, propionates, malonates, benzoates, and the like.

Suitable carrier materials include any carrier or vehicle commonly used as a base for creams, lotions, sprays, foams, gels, emulsions, lotions or paints for topical administration. Examples include emulsifying agents, inert carriers including hydrocarbon bases, emulsifying bases, non-toxic solvents or water-soluble bases. Particularly suitable examples include pluronics, HPMC, CMC and other cellulose-based ingredients, lanolin, hard paraffin, liquid paraffin, soft yellow paraffin or soft white paraffin, white beeswax, yellow beeswax, cetostearyl alcohol, cetyl alcohol, dimethicones, emulsifying waxes, isopropyl myristate, microcrystalline wax, oleyl alcohol and stearyl alcohol.

Preferably, the pharmaceutically acceptable carrier or vehicle is a gel, suitably a nonionic polyoxyethylene-polyoxypropylene copolymer gel, for example, a Pluronic gel, preferably Pluronic F-127 (BASF Corp.). This gel is particularly preferred as it is a liquid at low temperatures but rapidly sets at physiological temperatures, which confines the release of the agent to the site of application or immediately adjacent that site.

An auxiliary agent such as casein, gelatin, albumin, glue, sodium alginate, carboxymethylcellulose, methylcellulose, hydroxyethylcellulose or polyvinyl alcohol may also be included in the formulation of the invention.

Other suitable formulations include pluronic gel-based formulations, carboxymethylcellulose (CMC)-based formulations, and hydroxypropylmethylcellulose (HPMC)-based formulations. The composition may be formulated for any desired form of delivery, including topical, instillation, parenteral, intramuscular, subcutaneous, or transdermal administration. Other useful formulations include slow or delayed release preparations.

The formulation which is administered may contain transfection agents. Examples of such agents include cationic agents (for example calcium phosphate and DEAE-dextran) and lipofectants (for example Lipofectam™ and Transfectam™), and surfactants.

In one embodiment, the formulation further includes a surfactant to assist with polynucleotide cell penetration or the formulation may contain any suitable loading agent. Any suitable non-toxic surfactant may be included, such as DMSO. Alternatively a transdermal penetration agent such as urea may be included.

Optionally, the anti-connexin polynucleotide may be formulated with one or more therapeutic agents, agents useful for wound healing, and/or anti-fibrotic agents. In certain embodiments, one, two three, four, five or six therapeutic agents may be used in combination. In certain embodiments, one, two three, four, five or six agents useful for wound healing may be used in combination.

In one aspect, the one or more anti-connexin polynucleotides, either alone or in combination with one or more therapeutic agents and/or agents useful in wound healing are provided in the form of a wound dressing or matrix. In certain embodiments, the one or more anti-connexin polynucleotides (with or without one or more therapeutic agents or agents useful in wound healing) are provided in the four of a liquid, semi solid or solid composition for application directly, or the composition is applied to the surface of, or incorporated into, a solid contacting layer such as a dressing gauze or matrix. The wound dressing composition may be provided for example, in the form of a fluid or a gel. The one or more anti-connexin polynucleotides (with or without one or more therapeutic agents or agents useful in wound healing) may be provided in combination with conventional pharmaceutical excipients for topical application. Suitable carriers include: Pluronic gels, Polaxamer gels, Hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (Carbopols). Suitable carriers also include creams/ointments used for topical pharmaceutical preparations, e.g., creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilizers such as EDTA.

The effective dose for a given subject preferably lies within the dose that is therapeutically effective for at least 50% of the population, and that exhibits little or no toxicity at this level.

The effective dosage of each of the anti-connexin polynucleotides employed in the methods and compositions of the invention may vary depending on a number of factors including the particular anti-connexin polynucleotide employed, the mode of administration, the frequency of administration, the wound being treated, the severity of the wound being treated, the route of administration, the needs of a patient sub-population to be treated or the needs of the individual patient which different needs can be due to age, sex, body weight, relevant medical wound specific to the patient.

A suitable dose may be from about 0.001 to about 1 mg/kg body weight such as about 0.01 to about 0.4 mg/kg body weight. A suitable dose may however be from about 0.001 to about 0.1 mg/kg body weight such as about 0.01 to about 0.050 mg/kg body weight. Doses from about 1 to 100, 100-200, 200-300, 300-400, and 400-500 micrograms or more and up to about 500-1000 micrograms are appropriate. As noted herein, repeat applications are contemplated. Repeat applications are typically applied about once per week, or when healing may appear to be stalled or slowing.

Still other dosage levels between about 1 nanogram (ng)/kg and about 1 mg/kg body weight per day of each of the agents described herein. In certain embodiments, the dosage of each of the subject compounds will generally be in the range of about 1 ng to about 1 microgram per kg body weight, about 1 ng to about 0.1 microgram per kg body weight, about 1 ng to about 10 ng per kg body weight, about 10 ng to about 0.1 microgram per kg body weight, about 0.1 microgram to about 1 microgram per kg body weight, about 20 ng to about 100 ng per kg body weight, about 0.001 mg to about 100 mg per kg body weight, about 0.01 mg to about 10 mg per kg body weight, or about 0.1 mg to about 1 mg per kg body weight. In certain embodiments, the dosage of each of the subject compounds will generally be in the range of about 0.001 mg to about 0.01 mg per kg body weight, about 0.01 mg to about 0.1 mg per kg body weight, about 0.1 mg to about 1 mg per kg body weight, or about 1 mg per kg body weight. If more than one anti-connexin polynucleotide is used, the dosage of each anti-connexin polynucleotide need not be in the same range as the other. For example, the dosage of one anti-connexin polynucleotide may be between about 0.01 mg to about 1 mg per kg body weight, and the dosage of another anti-connexin polynucleotide may be between about 0.1 mg to about 1 mg per kg body weight. As noted herein, repeat applications are contemplated. Repeat applications are typically applied about once per week, or when wound-healing may appear to be stalled or slowing.

Other useful doses range from about 1 to about 10 micrograms per square centimeter of the size of the wound or the area to be treated. Certain doses will be about 1-2, about 1-5, about 2-4, about 5-7, and about 8-10 micrograms per square centimeter of the size of the wound or the area to be treated. Other useful doses are greater than about 10 micrograms per square centimeter of the size of the wound or the area to be treated, including about 15 micrograms per square centimeter of the size of the wound or the area to be treated, about 20 micrograms per square centimeter of the size of the wound or the area to be treated, about 25 micrograms per square centimeter of the size of the wound or the area to be treated, about 30 micrograms per square centimeter of the size of the wound or the area to be treated, about 35 micrograms per square centimeter of the size of the wound or the area to be treated, about 40 micrograms per square centimeter of the size of the wound or the area to be treated, about 50 micrograms per square centimeter of the size of the wound or the area to be treated, and about 100 micrograms per square centimeter of the size of the wound or the area to be treated. Other useful doses are about 150 micrograms per square centimeter of the size of the wound or the area to be treated, about 200 micrograms per square centimeter of the size of the wound or the area to be treated, about 250 micrograms per square centimeter of wound size, or about 500 micrograms per square centimeter of the size of the wound or the area to be treated. As noted herein, repeat applications are contemplated. Repeat applications are typically applied about once per week, or when wound-healing may appear to be stalled or slowing.

For example, in certain embodiments, the anti-connexin polynucleotide composition may be applied at about 0.01 micromolar ($\mu$M) or 0.05 $\mu$M to about 200 $\mu$M final concentration at the treatment site and/or adjacent to the treatment site. Preferably, the antisense polynucleotide composition is applied at about 0.05 $\mu$M to about 100 $\mu$M final concentration, more preferably, the anti-connexin polynucleotide composition is applied at about 1.0 $\mu$M to about 50 $\mu$M final concentration, and more preferably, the anti-connexin polynucleotide composition is applied at about 5-10 $\mu$M to about 30-50 $\mu$M final concentration. Additionally, the anti-connexin polynucleotide composition is applied at about 8 $\mu$M to about 20 $\mu$M final concentration, and alternatively the anti-connexin polynucleotide composition is applied at about 10 $\mu$M to about 20 $\mu$M final concentration, or at about 10 to about 15 $\mu$M final concentration. In certain other embodiments, the anti-connexin polynucleotide is applied at about 10 $\mu$M final concentration. In yet another embodiment, the anti-connexin polynucleotide composition is applied at about 1-15 $\mu$M final concentration. The dose at which an anti-connexin agent is administered to a patient will depend upon a variety of factors such as the age, weight and general condition of the patient, the condition that is being treated, and the particular anti-connexin agent that is being administered.

A suitable therapeutically effective dose of an anti-connexin agent may be from about 0.001 to about 1 mg/kg body weight such as about 0.01 to about 0.4 mg/kg body weight. A suitable dose may however be from about 0.001 to about 0.1 mg/kg body weight such as about 0.01 to about 0.050 mg/kg body weight.

Therapeutically effective doses of anti-connexin agents from about 1 to 100, 100-200, 100- or 200-300, 100- or 200- or 300-400, and 100- or 200- or 300- or 400-500 micrograms are appropriate. Doses from about 1-1000 micrograms are also appropriate. Doses up to 2 milligrams may also be used. Doses are adjusted appropriately when the anti-connexin agent or agents are provided in the form of a dressing, typically upward to maintain the desired total dose administration.

Alternatively, in the case of anti-connexin oligonucleotides, the dosage of each of the agents in the compositions may be determined by reference to the composition's concentration relative to the size, length, depth, area or volume of the area to which it will be applied. For example, in certain topical applications, dosing of the pharmaceutical compositions may be calculated based on mass (e.g. grams) of or the concentration in a pharmaceutical composition (e.g. $\mu$g/ul) per length, depth, area, or volume of the area of application. Useful doses range from about 1 to about 10 micrograms per square centimeter of wound size. Certain doses will be about 1-2, about 1-5, about 2-4, about 5-7, and about 8-10 micrograms per square centimeter of wound size. Other useful doses are greater than about 10 micrograms per square centimeter of wound size, including at least about 15 micrograms per square centimeter of wound size, at least about 20 micrograms per square centimeter of wound size, at least about 25 micrograms per square centimeter of wound size, about 30 micrograms per square centimeter of wound size, at least about 35 micrograms per square centimeter of wound size, at least about 40 micrograms per square centimeter of wound size, at least about 50 micrograms per square centimeter of wound size, and at least about 100 to at least about 150 micrograms per square centimeter of wound size. Other doses include about 150-200 micrograms per square centimeter, about 200-250 micrograms per square centimeter, about 250-300 micrograms per square centimeter, about 300-350 micrograms per square centimeter, about 350-400 micrograms per square centimeter, and about 400-500 micrograms per square centimeter.

In certain embodiments, the anti-connexin polynucleotide composition may be applied at about 0.01 micromolar ($\mu$M) or 0.05 $\mu$M to about 200 $\mu$M, or up to 300 $\mu$M or up to 1000 $\mu$M or up to 2000 $\mu$M or up to 3200 $\mu$M or more final concentration at the treatment site and/or adjacent to the treatment site, and any doses and dose ranges within these dose numbers. Preferably, the antisense polynucleotide composition is applied at about 0.05 $\mu$M to about 100 $\mu$M final concentration, more preferably, the anti-connexin polynucleotide composition is applied at about 1.0 $\mu$M to about 50 $\mu$M final concentration, and more preferably, the anti-connexin polynucleotide composition is applied at about 5-10 $\mu$M to about 30-50 $\mu$M final concentration. Additionally, the combined anti-connexin polynucleotide composition is applied at about 8 $\mu$M to about 20 $\mu$M final concentration, and alternatively the anti-connexin polynucleotide composition is applied at about 10 $\mu$M to about 20 $\mu$M final concentration, or at about 10 to about 15 $\mu$M final concentration. In certain other embodiments, the anti-connexin polynucleotide is applied at about 10 $\mu$M final concentration. In yet another embodiment, the anti-connexin polynucleotide composition is applied at about 1-15 $\mu$M final concentration. In other embodiments, the anti-connexin polynucleotide is applied at about a 20 $\mu$M, 30 $\mu$M, 40 $\mu$M, 50 $\mu$M, 60 $\mu$M, 70 $\mu$M, 80 $\mu$M, 90 $\mu$M, 100 $\mu$M., 10-200 $\mu$M, 200-300 $\mu$M, 300-400 $\mu$M, 400-500 $\mu$M, 500-600 $\mu$M, 600-700 $\mu$M, 700-800 $\mu$M, 800-900 $\mu$M, 900-1000 or 1000-1500 $\mu$M, or 1500 $\mu$M-2000 $\mu$M or 2000 $\mu$M-3000 $\mu$M or greater.

Anti-connexin polynucleotide dose amounts include, for example, about 0.1-1, 1-2, 2-3, 3-4, or 4-5 micrograms ($\mu$g), from about 5 to about 10 $\mu$g, from about 10 to about 15 $\mu$g, from about 15 to about 20 $\mu$g, from about 20 to about 30 $\mu$g, from about 30 to about 40 $\mu$g, from about 40 to about 50 $\mu$g, from about 50 to about 75 $\mu$g, from about 75 to about 100 $\mu$g, from about 100 µg to about 250 µg, and from 250 µg to about 500 µg. Dose amounts from 0.5 to about 1.0 milligrams or more or also provided, as noted above. Dose volumes will depend on the size of the site to be treated, and may range, for example, from about 25-100 µL to about 100-200 µL, from about 200-500 µL to about 500-1000 µL. Milliliter doses are also appropriate for larger treatment sites. As noted herein, repeat applications are contemplated. Repeat applications are typically applied about once per week, or when wound-healing may appear to be stalled or slowing.

Conveniently, the anti-connexin polynucleotide is administered in a sufficient amount to downregulate expression of a connexin protein, or modulate gap junction formation for at least about 0.5 to 1 hour, at least about 1-2 hours, at least about 2-4 hours, at least about 4-6 hours, at least about 6-8 hours, at least about 8-10 hours, at least about 12 hours, or at least about 24 hours post-administration.

The dosage of each of the anti-connexin polynucleotides in the compositions and methods of the subject invention may also be determined by reference to the concentration of the composition relative to the size, length, depth, area or volume of the area to which it will be applied. For example, in certain topical and other applications, e.g., instillation, dosing of the pharmaceutical compositions may be calculated based on mass (e.g. micrograms) of or the concentration in a pharmaceutical composition (e.g. µg/µl) per length, depth, area, or volume of the area of application.

The initial and any subsequent dosages administered will depend upon factors noted herein. Depending on the oligonucleotide, the dosage and protocol for administration will vary, and the dosage will also depend on the method of administration selected, for example, local or topical administration.

The doses may be administered in single or divided applications. The doses may be administered once, or application may be repeated. Typically, application will be repeated weekly until healing is promoted, or a repeat application may be made in the event that healing slows or is stalled. Doses may be applied 3-7 days apart, or more. Repeat applications may be made, for example, weekly, or bi-weekly, or monthly or in other frequency for example if and when wound healing slows or is stalled. For some indications, such as certain ocular uses, more frequent dosing, up to hourly may be employed.

Agents useful for wound healing suitable for the preparation of the pharmaceutical compositions described herein may be prepared and administered using methods as known in the art (see, for example, U.S. Pat. Nos. 7,098,190, 6,319,907, 6,331,298, 6,387,364, 6,455,569, 6,566,339, 6,696,433, 6,855,505, 6,900,181, 7,052,684 and EP 1100529 B1. The concentration of each anti-connexin polynucleotide and agent useful for wound healing need not be in the same range as the other. Other amounts will be known to those of skill in the art and readily determined. For example, suitable combination dosages and formulations in accordance with various aspects and embodiments as described herein may be administered according to the dosing regimen as described in U.S. Pat. No. 6,903,078 to Lewis entitled "Combination PDGF, KGF, IGF, and IGFBP for wound healing."

The initial and any subsequent dosages administered will depend upon the patient's age, weight, condition, and the disease, wound, disorder or biological condition being treated. Depending on the agent useful for wound healing, the dosage and protocol for administration will vary, and the dosage will also depend on the method of administration selected, for example, local or systemic administration.

The agent useful for wound healing may be applied internally or externally, and may be directed towards any tissue exhibiting a fibrotic lesion or area, or at risk thereof. For topical administration of IGF, for example, a zinc oxide formulation can be applied, which induces the local production of IGF, as described in Tarnow et al, *Scand J. Plast Reconstr Hand Surg.* 28: 255-259 (1994). An effective dose of PDGF has been reported to be 5 ng/mm$^2$ or higher when applied topically as described in U.S. Pat. No. 4,861,757, and at least 1 ng/ml local concentration of an isoform of PDGF (for example, PDGF-AA, PDGF-BB, or PDGF-AB), up to about 30 ng/ml local concentration applied to a population of fibroblasts as described in Lepisto et al., *Biochem Biophys Res. Comm* 209: 393-399 (1995). PDGF can be administered in a carboxymethylcellulose gel formulation at concentrations of about 10 µg/gm to about 500 µg/gm of gel, about 20 µg/gm to about 200 µg/gm, and about 30 µg/gm to about 100 µg/gm of gel, optimally about 100 µg/gm of gel. Efficacy of PDGF has been achieved within the range of about 3 µg/ml solution to about 300 µg/ml of solution administered.

About 50 µl of KGF of a concentration of about 5 µg/ml may be effective for wound healing by topical application to epithelial tissue as described in Sotozono et al, *Invest. Opthal. Vis. Science* 36: 1524-29 (1995). As described in U.S. Pat. No. 4,861,757, an effective amount of IGF when co-administered with PDGF is in the range of at least 2.5 ng/mm$^2$ to about 5 ng/mm$^2$, with a ratio of PDGF to IGF in the range of about 1:10 to about 25:1 weight to weight, with the most effective ratios being PDGF to IGF of about 1:1 to about 2:1 weight to weight. IGFBP administered in combination with IGF has been shown to increase wound healing at dose levels of about 5 µg of IGF with about 1.5 µg of phosphorylated IGFBP in a molar ration of about 11:1 IGF:IGFBP, as described in Jyung et al, *Surgery* 115:233-239 (1994).

For administration of polypeptide therapeutics, for example, PDGF, KGF, IGF and IGFBP polypeptides, the dosage can be in the range of about 5 µg to about 50 µg/kg of tissue to which the application is directed, also about 50 µg to about 5 mg/kg, also about 100 µg to about 500 µg/kg of tissue, and about 200 to about 250 µg/kg. For polynucleotide therapeutics, for example in a gene therapy administration protocol, depending on the expression strength the polynucleotide in the patient, for tissue targeted administration, vectors containing expressible constructs including PDGF, KGF, IGF, and IGFBP coding sequences can be administered in a range of about 100 ng to about 200 mg of DNA for local administration in a gene therapy protocol, also about 500 ng to about 50 mg, also about 1 µg to about 2 mg of DNA, about 5 µg of DNA to about 500 µg of DNA, and about 20 µg to about 100 µg during a local administration in a gene therapy protocol, and about 250 µg, per injection or administration. Factors such as method of action and efficacy of transformation and expression are therefore considerations that will effect the dosage required for ultimate efficacy for administration of DNA therapeutics. Where greater expression is desired, over a larger area of tissue, larger amounts of DNA or the same amounts re-administered in a successive protocol of administrations, or several administrations to different adjacent or close tissue portions of for example, a wound site may be required to effect a positive therapeutic outcome.

Therapeutic agents suitable for the preparation of the pharmaceutical compositions described herein may be formulated and administered using methods as known in the art. The initial and any subsequent dosages administered will depend upon the patient's age, weight, condition, and the disease, wound, disorder or biological condition being treated. Depending on the therapeutic, the dosage and protocol for administration will vary, and the dosage will also depend on the method of administration selected, for example, local or systemic administration.

As noted herein, the doses of either an anti-connexin polynucleotides or another agent administered in combination can be adjusted down from the doses administered when given alone.

The combined use of several agents may reduce the required dosage for any individual agent because the onset and duration of effect of the different agents may be complementary. In a preferred embodiment, the combined use of one or more anti-connexin polynucleotides and one or more therapeutic agents, agents useful for wound healing, and/or gap junction modifying agents has an additive, synergistic or super-additive effect.

In some cases, the combination of one or more anti-connexin polynucleotides and one or more therapeutic agents and/or one or more agents useful for wound healing have an additive effect. In other cases, the combination can have greater-than-additive effect. Such an effect is referred to herein as a "supra-additive" effect, and may be due to synergistic or potentiated interaction.

The term "supra-additive promotion of wound healing" refers to a mean wound healing produced by administration of a combination of an anti-connexin polynucleotide and one or more therapeutic agents and/or agents useful for wound healing, is statistically significantly higher than the sum of the wound healing produced by the individual administration of either any of the agents alone. Whether produced by combination administration of an anti-connexin polynucleotide and one or more therapeutic agents and/or agents useful for wound healing is "statistically significantly higher" than the expected additive value of the individual compounds may be determined by a variety of statistical methods as described herein and/or known by one of ordinary skill in the art. The term "synergistic" refers to a type of supra-additive inhibition in which both the anti-connexin polynucleotide and one or more therapeutic agents, agents useful for wound healing and/or gap junction modifying agents individually have the ability to promote wound healing or reduce fibrosis and scarring. The term "potentiated" refers to type of supra-additive effect in which one of the anti-connexin polynucleotide or one or more therapeutic agents and/or agents useful for wound healing individually has the increased ability to promote wound healing.

In general, potentiation may be assessed by determining whether the combination treatment produces a mean wound healing increase in a treatment group that is statistically significantly supra-additive when compared to the sum of the mean wound healing increases produced by the individual treatments in their treatment groups respectively. The mean wound healing increase may be calculated as the difference between control group and treatment group mean wound healing. The fractional increase in wound healing, "fraction affected" (Fa), may be calculated by dividing the treatment group mean wound healing increase by control group mean wound healing. Testing for statistically significant potentiation requires the calculation of Fa for each treatment group. The expected additive Fa for a combination treatment may be taken to be the sum of mean Fas from groups receiving either element of the combination. The Two-Tailed One-Sample T-Test, for example, may be used to evaluate how likely it is that the result obtained by the experiment is due to chance alone, as measured by the p-value. A p-value of less than 0.05 is considered statistically significant, that is, not likely to be due to chance alone. Thus, Fa for the combination treatment group must be statistically significantly higher than the expected additive Fa for the single element treatment groups to deem the combination as resulting in a potentiated supra-additive effect.

Whether a synergistic effect results from a combination treatment may be evaluated by the median-effect/combination-index isobologram method (Chou, T., and Talalay, P. (1984) Ad. Enzyme Reg. 22:27-55). In this method, combination index (CI) values are calculated for different dose-effect levels based on parameters derived from median-effect plots of the anti-connexin polynucleotide alone, the one or more agents useful for wound healing alone, and the combination of the two at fixed molar ratios. CI values of < 1 indicate synergy, CI-1 indicates an additive effect, and CP1 indicates an antagonistic effect. This analysis may be performed using computer software tools, such as CalcuSyn, Windows Software for Dose Effect Analysis (Biosoft (D, Cambridge UK).

Any method known or later developed in the art for analyzing whether a supra-additive effect exists for a combination therapy is contemplated for use in screening for suitable anti-connexin polynucleotides for use in combination with one or more therapeutic agents and/or agents useful for wound healing.

In another preferred embodiment, the combined use of one or more anti-connexin polynucleotides and one or more therapeutic agents and/or agents useful for wound healing reduces the effective dose of any such agent compared to the effective dose when said agent administered alone. In certain embodiments, the effective dose of the agent when used in combination with one or more anti-connexin polynucleotides is about $1/15$ to about $1/2$, about $1/10$ to about $1/3$, about $1/8$ to about $1/6$, about $1/5$, about $1/4$, about $1/3$ or about $1/2$ the dose of the agent when used alone.

In another preferred embodiment, the combined use of one or more anti-connexin polynucleotides and one or more therapeutic agents and/or agents useful for wound healing reduces the frequency in which said agent is administered compared to the frequency when said agent is administered alone. Thus, these combinations allow the use of lower and/or fewer doses of each agent than previously required to achieve desired therapeutic goals.

The doses may be administered in single or divided applications. The doses may be administered once, or application may be repeated.

One or more anti-connexin polynucleotides, either alone or in combination with one or more therapeutic agents and/or one or more agents useful in wound healing, may be administered by the same or different routes. The various agents of the invention can be administered separately at different times during the course of therapy, or concurrently in divided or single combination forms.

Preferably one or more anti-connexin polynucleotides useful in the treatment of fibrosis are delivered by topical administration (peripherally or directly to a site), including but not limited to topical administration using solid supports (such as dressings and other matrices) and medicinal formulations (such as gels, mixtures, suspensions and ointments). In one embodiment, the solid support comprises a biocompatible membrane or insertion into a treatment site. In another embodiment, the solid support comprises a dressing or matrix. In one embodiment of the invention, the solid support composition may be a slow release solid support composition, in which the one or more anti-connexin polynucleotides useful for wound healing is dispersed in a slow release solid matrix such as a matrix of alginate, collagen, or a synthetic bioabsorbable polymer. Preferably, the solid support composition is sterile or low bio-burden. In one embodiment, a wash solution comprising one or more anti-connexin polynucleotides can be used.

In another embodiment, lavage solution containing about 1 to about 100 µg/cm$^2$ (preferably about 10 to about 50 µg/cm$^2$) of an anti-connexin agent, would be used at the time of or immediately following injury or surgery. In all of the embodiments, other anti-connexin polynucleotides would be administered at equivalent doses adjusted for potency and tolerability of the polynucleotide.

The delivery of one or more anti-connexin polynucleotides (with or without one or more therapeutic agents or agents useful for wound healing) may occur over a period of time, in some instances for about 0.5 hours, 1-2 hours, about 2-4 hours, about 4-6 hours, about 6-8, or about 24 hours or longer, may be a particular advantage in more severe wounds. In some instances, cell loss may extend well beyond the site of a procedure to surrounding cells. Such loss may occur within 24 hours of the original procedure and is mediated by gap junction cell-cell communication. Administration of anti-connexin polynucleotide(s) will modulate communication between the cells and minimize additional cell loss or injury or consequences of injury.

While the delivery period will be dependent upon both the site at which the downregulation is to be induced and the therapeutic effect which is desired, continuous or slow-release delivery for about 0.5 hours, about 1-2 hours, about 2-4 hours, about 4-6 hours, about 6-8, or about 24 hours or longer is provided. In accordance with the present invention, this maybe achieved by inclusion of the anti-connexin polynucleotides (with or without one or more therapeutic agents or agents useful for wound healing) in a formulation together with a pharmaceutically acceptable carrier or vehicle, particularly in the form of a formulation for continuous or slow-release administration.

The routes of administration and dosages described herein are intended only as a guide since a skilled physician will determine the optimum route of administration and dosage for any particular patient.

Any of the methods of treating a subject having or suspected of having or a disease, disorder, or condition referenced or described herein may utilize the administration of any of the doses, dosage forms, formulations, and/or compositions herein described.

Dressings and Matrices

In one aspect, one or more anti-connexin polynucleotides either alone or in combination with one or more therapeutic agents useful in wound healing are provided in the form of a dressing or matrix. In certain embodiments, the one or more agents of the invention are provided in the faun of a liquid, semi solid or solid composition for application directly, or the composition is applied to the surface of, or incorporated into, a solid contacting layer such as a dressing gauze or matrix. The dressing composition may be provided for example, in the form of a fluid or a gel. One or more anti-connexin polynucleotides and one or more anti-connexin peptides or peptidomimetics may be provided in combination with conventional pharmaceutical excipients for topical application. Suitable carriers include: Pluronic gels, Polaxamer gels, Hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (Carbopols). Suitable carriers also include creams/ointments used for topical pharmaceutical preparations, e.g., creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilizers such as EDTA.

In addition to the biological matrices previously mentioned, suitable dressings or matrices may include, for example, the following with one or more anti-connexin polynucleotides and one or more other therapeutic agents.

1) Absorptives: suitable absorptives may include, for example, absorptive dressings, which can provide, for example, a semi-adherent quality or a non-adherent layer, combined with highly absorptive layers of fibers, such as for example, cellulose, cotton or rayon. Alternatively, absorptives may be used as a primary or secondary dressing.

2) Alginates: suitable alginates include, for example, dressings that are non-woven, non-adhesive pads and ribbons composed of natural polysaccharide fibers or xerogel derived from seaweed. Suitable alginates dressings may, for example, form a moist gel through a process of ion exchange upon contact with exudate. In certain embodiments, alginate dressings are designed to be soft and conformable, easy to pack, tuck or apply over irregular-shaped areas. In certain embodiments, alginate dressings may be used with a second dressing.

3) Antimicrobial Dressings: suitable antimicrobial dressings may include, for example, dressings that can facilitate delivery of bioactive agents, such as, for example, silver and polyhexamethylene biguanide (PHMB), to maintain efficacy against infection, where this is needed or desirable. In certain embodiments, suitable antimicrobial dressings may be available as for example, as sponges, impregnated woven gauzes, film dressings, absorptive products, island dressings, nylon fabric, non-adherent barriers, or a combination of materials.

4) Biological & Biosynthetics: suitable biological dressings or biosynthetic dressings may include, for example, gels, solutions or semi-permeable sheets derived from a natural source, e.g., pigs or cows. In certain embodiments, a gel or solution is applied to the treatment site and covered with a dressing for barrier protection. In another embodiment, a biological-based (e.g., pig intestinal mucosa or bladder tissue) or biosynthetic-based sheet is placed in situ which may act as membrane, remaining in place after a single application, or the may be biological dressings or biosynthetic dressings may be prepared in advance to include one or more, preferably two, anti-connexin agents.

5) Collagens: suitable collagen dressings may include, for example, gels, pads, particles, pastes, powders, sheets or solutions derived from for example, bovine, porcine or avian sources or other natural sources or donors. In certain embodiments, the collagen dressing may interact with treatment site exudate to form a gel. In certain embodiments, collagen dressing may be used in combination with a secondary dressing.

6) Composites: suitable composite dressings may include, for example, dressings that combine physically distinct components into a single product to provide multiple functions, such as, for example, a bacterial barrier, absorption and adhesion. In certain embodiment, the composite dressings are comprised of, for example, multiple layers and incorporate a semi- or non-adherent pad. In certain embodiment, the composite may also include for example, an adhesive border of non-woven fabric tape or transparent film. In certain other embodiment, the composite dressing may function as for example, either a primary or a secondary dressing and in yet another embodiment, the dressing may be used in combination with topical pharmaceutical composition.

7) Contact Layers: suitable contact layer dressings may include, for example, thin, non-adherent sheets placed on an area to protect tissue from for example, direct contact with other agents or dressings applied to the treatment site. In certain embodiments, contact layers may be deployed to conform to the shape of the area of the treatment site and are porous to allow exudate to pass through for absorption by an overlying, secondary dressing. In yet another embodiment, the contact layer dressing may be used in combination with topical pharmaceutical composition.

8) Elastic Bandages: suitable elastic bandages may include, for example, dressings that stretch and conform to the body contours. In certain embodiment, the fabric composition may include for example, cotton, polyester, rayon or nylon. In certain other embodiments, the elastic bandage may for example, provide absorption as a second layer or dressing, to hold a cover in place, to apply pressure or to cushion a treatment site.

9) Foams: suitable foam dressings may include, for example, sheets and other shapes of foamed polymer solutions (including polyurethane) with small, open cells capable of holding fluids. Exemplary foams may be for example, impregnated or layered in combination with other materials. In certain embodiment, the absorption capability may be adjusted based on the thickness and composition of the foam. In certain other embodiments, the area in contact with the treatment site may be non-adhesive for easy removal. In yet another embodiment, the foam may be used in combination with an adhesive border and/or a transparent film coating that can serve as an anti-infective barrier.

10) Gauzes & Non-Woven dressings: suitable gauze dressings and woven dressings may include, for example, dry woven or non-woven sponges and wraps with varying degrees of absorbency. Exemplary fabric composition may include, for example, cotton, polyester or rayon. In certain embodiment, gauzes and non-woven dressing may be available sterile or non-sterile in bulk and with or without an adhesive border. Exemplary gauze dressings and woven dressings may be used for cleansing, packing and covering a variety of treatment sites.

11) Hydrocolloids: suitable hydrocolloid dressings may include, for example, wafers, powders or pastes composed of gelatin, pectin or carboxymethylcellulose. In certain embodiment, wafers are self-adhering and available with or without an adhesive border and in a wide variety of shapes and sizes. Exemplary hydrocolloids are useful on areas that require contouring. In certain embodiments, powders and pastes hydrocolloids may use used in combination with a secondary dressing.

12) Hydrogels (Amorphous): suitable amorphous hydrogel dressings may include, for example, formulations of water, polymers and other ingredients with no shape, designed to donate moisture and to maintain a moist healing environments and or to rehydrate the treatment site. In certain embodiment, hydrogels may be used in combination with a secondary dressing cover.

13) Hydrogels: Impregnated Dressings: suitable impregnated hydrogel dressings may include, for example, gauzes and non-woven sponges, ropes and strips saturated with an amorphous hydrogel. Amorphous hydrogels may include for example, formulations of water, polymers and other ingredients with no shape, designed to donate moisture to a dry treatment site and to maintain a moist healing environment.

14) Hydrogel Sheets: suitable hydrogel sheets may include for example, three-dimensional networks of cross-linked hydrophilic polymers that are insoluble in water and interact with aqueous solutions by swelling. Exemplary hydrogels are highly conformable and permeable and can absorb varying amounts of drainage, depending on their composition. In certain embodiment, the hydrogel is non-adhesive against the treatment site or treated for easy removal.

15) Impregnated Dressings: suitable impregnated dressings may include, for example, gauzes and non-woven sponges, ropes and strips saturated with a solution, an emulsion, oil, gel or some other pharmaceutically active compound or carrier agent, including for example, saline, oil, zinc salts, petrolatum, xeroform and scarlet red as well as the compounds described herein.

16) Silicone Gel Sheets: suitable silicone gel sheet dressings may include, for example, soft covers composed of cross-linked polymers reinforced with or bonded to mesh or fabric.

17) Solutions: suitable liquid dressings may include, for example, mixtures of multiprotein material and other elements found in the extracellular matrix. In certain embodiment, exemplary solutions may be applied to the treatment site after debridement and cleansing and then covered with an absorbent dressing or a nonadherent pad.

18) Transparent Films: suitable transparent film dressings may include polymer membranes of varying thickness coated on one side with an adhesive. In certain embodiments, transparent films are impermeable to liquid, water and bacteria but permeable to moisture vapor and atmospheric gases. In certain embodiments, the transparency allows visualization of the treatment site.

19) Fillers: suitable filler dressings may include, for example, beads, creams, foams, gels, ointments, pads, pastes, pillows, powders, strands or other formulations. In certain embodiment, fillers are non-adherent and may include a time-released antimicrobial. Exemplary fillers may be useful to maintain a moist environment, manage exudate, and for treatment of for example, partial- and full-thickness wounds, infected wounds, draining wounds and deep wounds that require packing.

Treatment

The invention includes methods for treating and/or preventing, in whole or in part, various diseases, disorders and conditions, including, for example, methods of treating a subject having or suspected of having or predisposed to, or at risk for fibrosis, and various fibrotic diseases, disorders, or conditions characterized in whole or in part by (1) fibrous material, (2) excess production of fibrous material within the extracellular matrix, and/or (3) replacement of normal tissue elements by abnormal, non-functional, and/or excessive accumulation of matrix-associated components, comprising administering a composition comprising an anti-connexin polynucleotide and a pharmaceutically acceptable carrier or diluent. Preferred anti-connexin polynucleotides are anti-connexin 43 polynucleotides.

The invention includes methods for treating and/or preventing, in whole or in part, various diseases, disorders and conditions, including, for example, methods of treating a subject having or suspected of having or predisposed to, or at risk for fibrosis, comprising administering a composition comprising an anti-connexin polynucleotide, e.g., an anti-connexin 43 polynucleotide, and a pharmaceutically acceptable carrier or diluent.

The invention includes methods for treating and/or preventing, in whole or in part, various diseases, disorders and conditions, including, for example, methods of treating a subject having or suspected of having or predisposed to, or at risk for fibrosis, comprising administering a composition comprising an anti-connexin polynucleotide, e.g., an anti-connexin 43 polynucleotide, and a pharmaceutically acceptable carrier or diluent.

The invention includes methods for treating and/or preventing, in whole or in part, various diseases, disorders and conditions, including, for example, methods of treating a subject having or suspected of having or predisposed to, or at risk for pulmonary fibrosis, comprising administering a composition comprising an anti-connexin polynucleotide, e.g., an anti-connexin 43 polynucleotide, and a pharmaceutically acceptable carrier or diluent. In one embodiment, pulmonary fibrosis is diffuse interstitial pulmonary fibrosis. In another embodiment, the pulmonary fibrosis is glomerulosclerosis pulmonary fibrosis, idiopathic pulmonary fibrosis, silicosis, asbestosis, and chemotherapy/radiation induced pulmonary fibrosis.

The invention includes methods for treating and/or preventing, in whole or in part, various diseases, disorders and conditions, including, for example, methods of treating a subject having or suspected of having or predisposed to, or at risk for kidney fibrosis, comprising administering a composition comprising an anti-connexin polynucleotide, e.g., an anti-connexin 43 polynucleotide, and a pharmaceutically acceptable carrier or diluent. In one embodiment the kidney fibrosis is associated with glomerular sclerosis, renal tubulointerstitial fibrosis, or progressive renal disease. In one embodiment kidney fibrosis is associated with diabetic neuropathy.

The invention includes methods for treating and/or preventing, in whole or in part, various diseases, disorders and conditions, including, for example, methods of treating a subject having or suspected of having or predisposed to, or at risk for liver fibrosis, comprising administering a composition comprising an anti-connexin polynucleotide, e.g., an anti-connexin 43 polynucleotide, and a pharmaceutically acceptable carrier or diluent. In one embodiment the liver fibrosis arises from chronic liver injury. In one embodiment, liver fibrosis is associated with haemochromatosis, Wilson's disease, alcoholism, schistosomiasis, viral hepatitis, bile duct obstruction, exposure to toxins, and metabolic disorders.

The invention includes methods for treating and/or preventing, in whole or in part, various diseases, disorders and conditions, including, for example, methods of treating a subject having or suspected of having or predisposed to, or at risk for liver cirrhosis, comprising administering a composition comprising an anti-connexin polynucleotide, e.g., an anti-connexin 43 polynucleotide, and a pharmaceutically acceptable carrier or diluent.

The invention includes methods for treating and/or preventing, in whole or in part, various diseases, disorders and conditions, including, for example, methods of treating a subject having or suspected of having or predisposed to, or at risk for cardiac fibrosis, comprising administering a composition comprising an anti-connexin polynucleotide, e.g., an anti-connexin 43 polynucleotide, and a pharmaceutically acceptable carrier or diluent. In one embodiment, the cardiac fibrosis is endocardial fibrosis. In another embodiment, the cardiac fibrosis is endomyocardial fibrosis.

The invention includes methods for treating and/or preventing, in whole or in part, various diseases, disorders and conditions, including, for example, methods of treating a subject having or suspected of having or predisposed to, or at risk for oral submucous fibrosis, comprising administering a composition comprising an anti-connexin polynucleotide, e.g., an anti-connexin 43 polynucleotide, and a pharmaceutically acceptable carrier or diluent.

The invention includes methods for treating and/or preventing, in whole or in part, various diseases, disorders and conditions, including, for example, methods of treating a subject having or suspected of having or predisposed to, or at risk for retroperitoneal fibrosis, comprising administering a composition comprising an anti-connexin polynucleotide, e.g., an anti-connexin 43 polynucleotide, and a pharmaceutically acceptable carrier or diluent.

The invention includes methods for treating and/or preventing, in whole or in part, various diseases, disorders and conditions, including, for example, methods of treating a subject having or suspected of having or predisposed to, or at risk for deltoid fibrosis, comprising administering a composition comprising an anti-connexin polynucleotide, e.g., an anti-connexin 43 polynucleotide, and a pharmaceutically acceptable carrier or diluent.

The invention includes methods for treating and/or preventing, in whole or in part, various diseases, disorders and conditions, including, for example, methods of treating a subject having or suspected of having or predisposed to, or at risk for acute fibrosis, comprising administering a composition comprising an anti-connexin polynucleotide, e.g., an anti-connexin 43 polynucleotide, and a pharmaceutically acceptable carrier or diluent. In certain embodiments, the acute fibrosis is associated with various forms of trauma including, for example, accidental injuries, infections, radiation or chemotherapy treatments.

The invention includes methods for treating and/or preventing, in whole or in part, various diseases, disorders and conditions, including, for example, contracture or recurrence thereof, comprising administering a effective amount of a composition comprising an anti-connexin polynucleotide. In one embodiment the contracture is capsular contracture, Dupytren's contracture, Volkmann's contracture, Ledderhose's contracture, Peyronie's contracture. In one embodiment, the composition is administered to the site of the injury before, at the time of and/or after a release procedure (e.g., forced manipulation, open release, arthroscopic release, or debulking of scar) to prevent the recurrence of scarred and abnormal tissue and/or further contracture.

In one embodiment any one of the methods of treatment described herein further comprises administration of second composition having one or more drugs effective in preventing and/or decreasing fibrosis or fibrotic tissue. In one aspect the second composition comprises one or more anti-connexin polynucleotides, e.g., one or more anti-connexin 43 polynucleotides. In one aspect the second composition comprises one or more therapeutic agents. In another aspect of the invention, the second composition comprises one or more agents useful for wound healing. In another aspect of the invention, the second composition comprises one or more one or more therapeutic agents.

When not administered as a fixed combination, preferred methods include the sequential administration of one or more anti-connexin polynucleotides and one or more therapeutic agents and/or agents useful for wound healing. Preferably, the polynucleotides and agents are administered sequentially within at least about one-half hour of each other. The polynucleotides and agents may also be administered with about one hour of each other, with about one to two or three days to about one week of each other, or as otherwise deemed appropriate. Preferably, the anti-connexin polynucleotide is administered first.

In another embodiment for treatment of fibrosis and fibrotic disaeses, disorders and conditions, either or both of the one or more anti-connexin polynucleotides and one or more threapeutic agents and/or agents useful for wound healing are provided in amounts or doses that are less that those used when the polynucleotides or agents are administered alone, i.e., when they are not administered in combination. Such lesser amounts of agents administered are typically from about one-twentieth to about one-tenth the amount or amounts of the agent when administered alone, and may be about one-eighth the amount, about one-sixth the amount, about one-fifth the amount, about one-fourth the amount, about one-third the amount, and about one-half the amount when administered alone.

Compositions

The present invention is directed to pharmaceutical compositions and formulations useful in treating or preventing fibrosis and fibrotic diseases, disorders and conditions, wherein the composition or formulation comprises therapeutically effective amounts of an anti-connexin polynucleotide, such as a connexin antisense polynucleotide.

Equally, in instances of other tissue damage the methods, compositions and formulations of the invention are effective in treating or preventing fibrosis. The compositions and formulations, therefore, have clear benefit in the treatment of fibrosis and fibrotic conditions.

In one preferred form, the composition contains one or more anti-connexin polynucleotides, for example a connexin antisense polynucleotide, to the mRNA of one connexin protein only. Most preferably, this connexin protein is connexin 43.

Alternatively, the compositions may comprise polynucleotides to more than one connexin protein. Preferably, one of the connexin proteins to which polynucleotides are directed is connexin 43. Other connexin proteins to which oligodeoxynucleotides are directed may include, for example, connexins 26, 30, 31.1, 32, and 37. Suitable exemplary polynucleotides (and ODNs) directed to various connexins are set forth in Table 1.

Many aspects of the invention are described with reference to oligodeoxynucleotides. However it is understood that other suitable polynucleotides (such as RNA polynucleotides) may be used in these aspects. Other anti-connexin oligonucleotides are RNAi and siRNA oligonucleotides.

Accordingly, in one aspect, the invention provides compositions for use in therapeutic treatment, which comprises at least one anti-connexin polynucleotide, preferably an anti-connexin 43 polynucleotide. In a preferred embodiment, the composition further comprises a pharmaceutically acceptable carrier or vehicle.

Kits, Medicaments and Articles of Manufacturer

In one aspect, the invention provides a kit for preventing or treating fibrosis.

The kit may include one or more compositions described herein. For example, the kit may include a composition comprising an effective amount of one or more anti-connexin polynucleotides, e.g., an anti-connexin 43 polynucleotides, effective for the treatment of a subject having, at risk for, or predisposition to a fibrotic disease, disorder or condition. In one embodiment, the kit comprises a composition that comprises an effective amount of one or more polynucleotide homologues effective for the treatment of a subject having, at risk for, or predisposition to a fibrotic disease, disorder or condition.

Optionally, one or more anti-connexin polynucleotides may also be used in the manufacture of the medicament useful for the treatment of a subject having, at risk for, or predisposition to a fibrotic disease, disorder or condition. In one embodiment, the medicament comprises a therapeutically effective amount of an anti-connexin polynucleotide, preferably an anti-connexin 43 polynucleotide, and a pharmaceutically acceptable carrier.

In another aspect, the invention includes an article of manufacture comprising a vessel containing an effective amount of one or more anti-connexin polynucleotides, e.g., an anti-connexin 43 polynucleotide, and instructions for use, including use for the treatment of a subject having, at risk for, or predisposition to a fibrotic disease, disorder or condition.

Thus, in accordance with the invention, there are provided compounds, compositions, formulations by which cell-cell communication can be regulated or down-regulated in a transient and site-specific manner. The formulations therefore have application in methods of therapy and in other treatments.

In instances of tissue damage or fibrosis, the compounds, compositions and formulations of the invention will be effective in both preventing fibrosis and promoting the healing process where needed. The formulations therefore will have benefit in the prevention of fibrosis, whether the result of external trauma or disease state, for example.

A better understanding of the invention will be gained by reference to the following experimental section. The following experiments are illustrative and are not intended to limit the invention or the claims in any way.

EXAMPLES

Example 1

This example demonstrates a method for qualitative and quantitiative evaluation of anti connexin agents and their ability to inhibit fibrosis. Rats are injected either with anti-thymocyte serum (ATS) (see S. Okuda et al., *J. Clin. Invest.*, Vol. 86, (1990, pp. 453-462) to induce glomerulonephritis or with phosphate buffered saline (PBS) to serve as controls. Six days later, the kidneys are removed, and the glomeruli are isolated and placed in culture for 72 hours. Culture conditions consist of 2000 glomeruli/well in a 2 ml volume of serum-free RPMI 1640 (with insulin supplementation) (Gibco; Gaithersburg, Md.). Test anti-connexin polynucleotides are added at the time of the culture. The supernatant from the cultures is collected and stored at −70° C. until assayed to determine the concentration of collagen I, transforming growth factor β-1 (TGFβ-1), fibronectin containing an extra domain A (fibronectin EDA+), and plasminogen activator inhibitor I 9PAI-I) as markers of fibrotic activity. In addition, individual glomeruli are examined by immunofluorescent staining and scored for relevant matrix proteins. Values are compared between PBS-treated, negative fibrotic control glomeruli; ATS-treated, non-drug treated, positive fibrotic control glomeruli; and the ATS-treated, drug treated, fibrotic glomeruli to determine the degree to which the fibrotic process is inhibited by the anti-connexin polynucleotide.

Example 2

This example demonstrates a method for testing anti connexin agents and their ability to inhibit fibrosis. Rats are injected either with anti-thymocyte serum (ATS) to induce glomerulonephritis or with phosphate buffered saline (PBS) as a control. One hour later, treatment is initiated with anti-connexin polynucleotide. Anti-connexin polynucleotides are administered subcutaneously twice per day for 5 days. On day 5 the rats are placed in metabolic cages, and 24 hour urine is collected to determine protein content. On day 6, the kidneys are removed, and tissue samples are either placed in formalin or frozen for histological evaluation. Glomeruli are isolated from the remaining tissue and are placed in culture for 72 hours. Culture conditions consist of 2000 glomeruli/well in a 1 ml volume of serum free RPMI 1640 (with insulin supplementation). The supernatant from the cultures are collected and stored at −70° C., until assayed to determine the concentration of collagen I, transforming growth factor β-1 (TGF β-1), fibronectin containing an extra domain A (fibronectin EDA+), and plasminogen activator inhibitor 1 (PAI1) as markers of fibrotic activity. The presence of matrix proteins is measured via immunofluorescent staining of frozen kidney sections with antibodies to matrix proteins induced by TGF β-1 such as fibronectin EDA+, collagen I, PAI1 and tenasin. From the cultured isolated glomeruli direct measurements of TGF β-1, PAI1 and fibronectin secreted into the culture supernatant can be determined via ELISAs (enzyme-linked immunoabsorbent assay). Glomeruli from samples in each group can be used to extract mRNA and the message levels for TGF β-1, GADPH, collagen I, collagen III, Fibronectin, and PAI1 determined by Northern analysis. As an indicator of gross histological changes, PAS (periodic acid-Schiff) stained paraffin sections are graded on the basis of their pathological matrix scores. Values are compared between PBS-treated, negative fibrotic control animals; ATS-treated, non-drug treated, drug-treated animals to determine the degree to which the fibrotic process is inhibited by the anti-connexin polynucleotide.

Example 3

Wounds are created in C57BL6/KsJ db/db mice with a 4 mm biopsy punch. The mice may be obtained from The Jackson Laboratories and are typically aged 3-7 months before the onset of the wounding protocol. All mice are anesthetized prior to wounding. Two wounds are introduced onto the upper back of each animal by pulling the skin away from underlying structures and pushing the punch through the isolated skin. Typically, wounds are created to an average depth of 1.7 mm, with a range of 1.3 to 2.2 mm. No muscle involvement occurred during the course of wounding. Immediately post-wounding the wounds are either treated with normal saline (to serve as the non treated control group) or with suitable test anti-connexin polynucleotide.

Each day the wounds are digitally photographed and wound areas are determined by computer integration of the photographs. All wound treatments and the subsequent data analysis are performed in a blind manner. Wound area at the time of wounding (day 0) is set to a relative value of 1 for all wounds; such that subsequent wound areas are converted to relative wound areas by dividing the wound area at day "n" by the wound area at day zero.

TAnti-fibrotic efficacy based on the application of a single dose of the anti-connexin polynucleotide (at the time of wounding, day zero) as determined by the time to full wound closure in a mouse model is determined.

Endpoints such as fibrosis, wound closure, wound contraction, and inflammation are assessed starting at day one post wounding and continues for a pre-determined period of time (e.g. hours, days, weeks, months or years).

Example 4

The anti-fibrotic efficacy of anti-connexin polynucleotide is assessed in a mouse model of fibrosis treatment. Suitable numbers of adult mice are divided into statistically meaningful sample size groups (e.g. six groups in groups of eight): four treated and four control. The mice are anaesthetized using IP injection of Avertine, the dorsal surface shaved and two 1 cm incisions made through the skin down to and including the panniculus carnosus muscle at specific anatomical positions. The wounds are left unsutured and the animals returned to individual cages. Group of animals are killed after 1 day (d), 3 d, 5 d, 7 d, 14 and 70 d post-wounding and the wounds harvested. Half of each harvested wound is fixed in formal saline and the other half embedded in OCT medium and frozen over liquid nitrogen. Photographic records are kept of the wounds at each time point to enable comparison of microscopic and macroscopic results.

Histological Assessment: Haematoxylin and Eosin (H&E) and Masson's Trichrome stains are used to determine the cellularity and collagen content of the wounds respectively.

Scoring of Fibrosis: At 70 Days Post Wounding, the histology slides are scored using a Visual Analogue Scale (VAS) consisting of a 10 cm line where 0 represents normal skin and 10 an extreme case of fibrosis. A ranking scale is also used wherein 0 represents normal skin and 5 an extreme fibrotic skin. The ranking of 3 is used for the score of a control fibrosis.

Immunohistochemistry: Samples from 1, 3, 5 and 7 day wounds are stained using several antibodies including: 1) Anti-mouse fibronectin or 2) TRITC-labelled phalloidin. Phalloidin is extracted from the mushroom *amanita phalloides* and binds to filamentous actin (F-actin) so is useful in localizing and distinguishing between extra- and intracellular F-actin.

Image Analysis: Image analysis is carried out using PC based image capture system ('PC Image') and the following parameters are measured in order to quantify differences in the anti-fibrotic efficacy of the test agent between test and control wounds: 1) Wound width (both linear between wound edges and actual perimeter); 2) Retraction of the panniculus carnosus muscle; 3) Mid-wound width; 4) Re-epithelialization; 5) Fibrosis width at 3 points: base, middle and top; and 6) Thickness of new epithelium.

All wounds are measured for wound width and retraction of the panniculus carnosus muscle, the other measurements are taken at appropriate time points. Statistical analysis of the measurements is performed using suitable statistical software well-known and widely available in the art. Exemplary statistical tests may include Mann-Whitney U test and the Kolgomorov-Smirnov test to compare results from the control and test animals.

Histology: Histological assessment and endpoints for fibrosis may include, for example, evidence of neovasculorisation and collagen formation in the wound area; inflammation, level of new collagen formation; local accumulation of hair follicles immediately adjacent to and surrounding the fibrosis; and improvements in the quality of fibrotic tissue.

Example 5

This example describes and internal wound healing dressing/film comprising encapsulation of anti-connexin polynucleotides in Ethylene Vinyl Acetate Films and Polycaprolactone Paste.

Suitable amounts of an exemplary anti-connexin polynucleotide and 45 mg of ethylene vinyl acetate (EVA, molecular weight approximately 50 k, Polysciences) are dissolved/suspended in 1 ml of dichloromethane. Two hundred μl of the solution is pipetted onto 1 cm diameter teflon discs and allowed to dry overnight (solvent evaporation) to form thin elastic films to give approximately 10 mg films with an approximate thickness of 100 μm.

The rate of drug release from these films is measured by placing 5 mg sections of films in 20 ml capped glass tubes containing 10 ml of phosphate buffered saline (PBS) pH 7.4. The tubes are capped, and placed in an orbital shaker at 37° C. At specified times, the tubes are removed and the amount of drug released is analysed by absorbance spectroscopy. This and/or other exemplary dosage form of anti-connexin polynucleotide represents a biocompatible, biodegradable, injectable formulation of the drug that releases the drug in a controlled manner.

PCL paste: exemplary anti-connexin polynucleotide is blended into polycaprolactone (PCL, Birmingham polymers, molecular weight 54K) at 60° C. by spatula levigation at a concentration of 10% w/w. This mixture is then pipetted into 1 ml plastic syringes and allowed to cool. This formulation could be injected through an 18 gauge needle at 56° C.

To measure drug release from the PCL paste, 10 mg aliquots of molten paste are injected onto the base of 15 ml glass tubes and allowed to cool and set. Fifteen ml of PBS is added to each tube and the tubes are capped, and tumbled end over end in a 37° C. oven. At specified times, the tubes are removed and the amount of drug released is analysed by absorbance spectroscopy. The release profile of the anti-connexin polynucleotide is obtained. This and/or other exemplary dosage form of anti-connexin polynucleotide represents a biocompatible, biodegradable, injectable formulation of the drug that releases the drug in a controlled manner.

Example 6

This example describes membranes loaded with anti-connexin polynucleotides.

Medical grade sodium hyaluronate is obtained from Lifecore Scientific. All solvents are HPLC grade and obtained from Fisher. Plastic Petri dishes are obtained from Fisher Scientific. Ethyl-3-(dimethylamino) carbodiimide (EDAC) and anti-connexin polynucleotide are prepared as described elsewhere throughout the instant disclosure.

Preparation of Films. Anti-Connexin Polynucleotide Loaded Films are Made by preparing an exemplary solution of 0.6% w/v anti-connexin polynucleotide, 0.4% w/v sodium hyaluronate and 0.15% w/v glycerol in water. Control films (no anti-connexin polynucleotide) are made by preparing a solution or mixture of 0.4% w/v sodium hyaluronate and 0.15% w/v glycerol in water. Anti-connexin polynucleotide loaded films and control films are cast from these solutions by pipetting 4 g of each solution into separate 2.5 cm diameter plastic Petri dishes and drying for 24 hours at 60° C. The crosslinking agent EDAC is included at 4 mM (final concentration). Each dried film is then carefully removed from the Petri dish using a surgical blade.

Sterilization. Films are packed between 5 cm×5 cm weighing paper (Fisher scientific) and heat sealed in plastic bags. Films are then terminally sterilized using gamma irradiation from a cobalt-60 source and exposed to 2.5 Mrad of radiation with cooling of the sealed tube on ice.

Example 7

This example describes an external wound dressing comprising an anti-connexin polynucleotide. Drug loading into fatty acid (e.g. fish oil) derived membranes for wound dressing. Pure fish oil is heated at 200° F. to obtain a viscosity of 15,000-20,000 cps at 24° C. to form a pre-treated or pre-thickened fish oil. 3.1 g of the pre-treated or pre-thickened fish oil is then mixed with an appropriate amount of an exemplary anti-connexin polynucleotide. The mixture is then heated gently to allow the anti-connexin polynucleotide to dissolve in the fish oil. This resulted in an anti-connexin polynucleotide in fish oil formulation by weight. After heating, the mixture is cast onto a Teflon mat with a casting knife to form a thin film. The thin film is then placed under a UV lamp for 15 minutes. After exposure to UV light, the thin film is heated in an oven to heat cure, after which the thin film is removed from the oven and allowed to cool for 1 hour. After the thin film is cooled, it is peeled from the Teflon mat to form a stand-alone film. The resultant film had a thickness of approximately 0.005". Drug extraction and dissolution are performed on the film by high performance liquid chromatography (HPLC). The extraction result can indicate amout of drug loading per film sample length. In general, the dissolution of the anti-connexin polynucleotide should release the drug in an approximately linear fashion as a function of time.

Example 8

This example describes overlaying a drug-loaded fish oil on a stand-alone film for use in treating or preventing fibrosis. Pure fish oil is heated to obtain a viscosity greater than 100,000 cps at 24° C. to form the pre-cured fish oil film. 3.33 g of pre-cured fish oil is mixed with an appropriate amount of anti-connexin polynucleotide to form a mixture. This resulted in a fish oil formulation. After the anti-connexin polynucleotide is solubilized in the pre-cured fish oil, the mixture is brushed onto a 1" by 1½ piece of stand-alone film. The film with the drug coating is then heated. Drug extraction and dissolution are performed on the film by HPLC. The extraction result can indicate amout of drug loading per film sample length. In general, the dissolution of the anti-connexin polynucleotide should release the drug in an approximately linear fashion as a function of time.

Example 9

This example describes drug coating by allowing a stand-alone wound covering film to swell with a solution including a therapeutic anticonnexin agent. Suitable amounts of anti-connexin polynucleotides are mixed with suitable amounts of EtOH. This resulted in a % formulation by weight. A 1" by 1½" of stand-alone film is dipped into the anti-connexin polynucleotide formulation and allowed to swell. The stand-alone film is then allowed to air dry. The resultant film is approximately 0.005" in thickness. Drug extraction and dissolution are performed on the film by HPLC. The extraction result can indicate amout of drug loading per film sample length. In general, the dissolution of the anti-connexin polynucleotide should release the drug in an approximately linear fashion as a function of time.

Example 10

Anti-connexin agent is conveniently formulated in a form suitable for administration according to the methods of the present invention.

Suitable formulations include a mixture of the following formulating agents. The amount of the individual anti-connexin agent or agents and formulating agents will depend on the particular use intended.

ASO in PBS
Polyquarternium 10
HEC/HPMC/CMC
Na Hyaluronate
Tween 20
Poloxamer 188
Pluronic 87 NF
SLES
Poly L-lysine/Polyethylene Imine
Banzalkonium chloride -continued Methyl paraben
Propl paraben
Propylene Glycol
10 mM Phosphate Buffer Example 11

Formulations for use according to methods of the present invention are prepared by mixing the compounds in the proportions noted below. In one preferred embodiment, the anti-connexin agent is an anti-connexin polynucleotide. In other embodiments, the anti-connexin polynucleotide is an anti-sense oligonucleotide, for example, an anti-sense oligonucleotide of SEQ. ID. NO. 1

Formulation A

Made up of the following materials (% w/w)—Anti-connexin agent in phosphate-buffered saline (0.47%); Methylparaben (0.17%); Propylparaben (0.03%); Propylene Glycol (1.5%); HPMC (1.5%); and 10 mM Phosphate Buffer (96.33%). Formulation is a clear gel with pH ~6.74 and osmolality of 244.

Formulation B

Made up of the following materials (% w/w)—Anti-connexin agent in phosphate-buffered saline (0.47%); Methylparaben (0.17%); Propylparaben (0.03%); Propylene Glycol (1.5%); HPMC (1.5%); 0.5% BAC (0.1%); and 10 mM Phosphate Buffer (96.23%). Formulation is a clear gel with pH ~6.65 and osmolality of 230.

Formulation C

Made up of the following materials (% w/w)—Anti-connexin agent in phosphate-buffered saline (0.47%); Methylparaben (0.17%); Propylparaben (0.03%); Propylene Glycol (1.5%); HPMC (1.5%); Polyquaternium 10 (0.5%); Poloxamer 188 (0.1%); and 10 mM Phosphate Buffer (95.73%). Formulation is a slightly hazy gel with pH ~6.59 and osmolality of 233.

Formulation D

Made up of the following materials (% w/w)—Anti-connexin agent in phosphate-buffered saline (0.47%); Methylparaben (0.17%); Propylparaben (0.03%); Propylene Glycol (1.5%); HPMC (1.5%); SLES (0.5%); and 10 mM Phosphate Buffer (95.83%). Formulation is a clear gel with pH ~6.8 and osmolality of 246.

Formulation E

Made up of the following materials (% w/w)—Anti-connexin agent in phosphate-buffered saline (0.47%); Methylparaben (0.17%); Propylparaben (0.03%); Propylene Glycol (1.5%); HPMC (1.5%); Poloxamer 188 (0.1%); 25K Polyethylene Imine (0.075%); and 10 mM Phosphate Buffer (96.155%). Formulation is a hazy gel with pH ~7.8 and osmolality of 249.

Formulation F

Made up of the following materials (% w/w)—Anti-connexin agent in phosphate-buffered saline (0.47%); Methylparaben (0.17%); Propylparaben (0.03%); Propylene Glycol (1.5%); HPMC (1.5%); Sodium Hyaluronate (0.1%); and 10 mM Phosphate Buffer (96.23%). Formulation is a clear gel with pH ~6.88 and osmolality of 289.

Formulation G

Made up of the following materials (% w/w)—Anti-connexin agent in phosphate-buffered saline (0.47%); Methylparaben (0.17%); Propylparaben (0.03%); Propylene Glycol (1.5%); Sodium Hyaluronate (1.0%); and 10 mM Phosphate Buffer (96.83%). Formulation is a clear gel with pH ~6.81 and osmolality of 248.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and subgeneric groupings falling within the generic disclosure also faun part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and applicants reserve the right to revise the application or claims to refer specifically to any individual member or any subgroup of members of the Markush group.

Other embodiments are within the following claims. The patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention claimed is:

1. A method of preventing or decreasing excessive accumulation of fibrous material within the extracellular matrix in injured or damaged tissue of a subject comprising identifying a subject in need thereof, and administering to the subject an anti-connexin 43 polynucleotide, thereby preventing or decreasing excessive accumulation of fibrous material within the extracellular matrix in said tissue of said subject, wherein the tissue is skin tissue, brain tissue, nerve tissue, lung tissue, cardiac tissue, kidney tissue, or liver tissue.

2. The method of claim 1, wherein the anti-connexin 43 polynucleotide decreases connexin 43 protein expression.

3. The method of claim 1 wherein the anti-connexin 43 polynucleotide is an antisense oligonucleotide.

4. The method of claim 1 wherein the anti-connexin 43 polynucleotide is an siRNA oligonucleotide.

5. The method of claim 1 wherein the anti-connexin 43 polynucleotide is an RNAi oligonucleotide.

6. The method of claim 1 wherein the anti-connexin 43 polynucleotide is administered to prevent or retard fibrosis.

7. The method of claim 1 wherein the subject has pulmonary fibrosis.

8. The method of claim 7, wherein the pulmonary fibrosis is selected from the group consisting of diffuse interstitial pulmonary fibrosis, glomerulosclerosis pulmonary fibrosis, idiopathic pulmonary fibrosis, silicosis, asbestosis, and chemotherapy/radiation induced pulmonary fibrosis.

9. The method of claim 1, wherein the subject has kidney fibrosis.

10. The method of claim 9, wherein the kidney fibrosis is associated with glomerular sclerosis, renal tubulointerstitial fibrosis, progressive renal disease, diabetic neuropathy.

11. The method of claim 1, wherein the subject has liver fibrosis.

12. The method of claim 11, wherein the liver fibrosis arises from chronic liver injury.

13. The method of claim 11, wherein the liver fibrosis is associated with haemochromatosis, Wilson's disease, alcoholism, schistosomiasis, viral hepatitis, bile duct obstruction, exposure to toxins, and metabolic disorders.

14. The method of claim 1, wherein the subject has cardiac fibrosis.

15. The method of claim 14, wherein the cardiac fibrosis is endocardial fibrosis or endomyocardial fibrosis.

16. The method of claim 1, wherein the subject has oral submucous fibrosis, retroperitoneal fibrosis, or deltoid fibrosis.

17. The method of claim 1, wherein the subject has acute fibrosis.

18. The method of claim 17, wherein the acute fibrosis is associated an accidental injury, an infection, or radiation or chemotherapy treatments.

19. The method of claim 1, wherein the subject has a disease, disorder or condition selected from the group consisting of scleroderma, pancreatitis, inflammatory bowel disease, Crohn's disease, nodular facilitis, and eosinophilic facititis.

20. The method of claim 19, wherein the scleroderma is morphea, generalized morphea, or linear scleroderma.

21. The method of claim 1, wherein the connexin 43 is human connexin 43.

22. A method of claim 1 wherein the anti-connexin 43 polynucleotide is administered in a contact layer dressing for placement in situ to prevent undesired fibrosis.

23. The method of claim 1, wherein the anti-connexin 43 polynucleotide comprises a sequence selected from SEQ ID NOs:1 to 3.

* * * * *

SEQUENCE LISTING

```
<160> NUMBER OF SEQ ID NOS: 12

<210> SEQ ID NO 1
<211> LENGTH: 30
<212> TYPE: DNA
<213> ORGANISM: Artificial
<220> FEATURE:
<223> OTHER INFORMATION: Mammalian-derived

<400> SEQUENCE: 1
gtaattgcgg caagaagaat tgtttctgtc                                    30

<210> SEQ ID NO 2
<211> LENGTH: 30
<212> TYPE: DNA
<213> ORGANISM: artificial
<220> FEATURE:
<223> OTHER INFORMATION: Mammalian-derived

<400> SEQUENCE: 2
gtaattgcgg caggaggaat tgtttctgtc                                    30

<210> SEQ ID NO 3
<211> LENGTH: 30
<212> TYPE: DNA
<213> ORGANISM: artificial
<220> FEATURE:
<223> OTHER INFORMATION: Mammalian-derived

<400> SEQUENCE: 3
ggcaagagac accaaagaca ctaccagcat                                    30

<210> SEQ ID NO 4
<211> LENGTH: 27
<212> TYPE: DNA
<213> ORGANISM: artificial
<220> FEATURE:
<223> OTHER INFORMATION: Mammalian-derived

<400> SEQUENCE: 4
```

-continued

```
tcctgagcaa tacctaacga acaaata                                    27

<210> SEQ ID NO 5
<211> LENGTH: 20
<212> TYPE: DNA
<213> ORGANISM: artificial
<220> FEATURE:
<223> OTHER INFORMATION: Mammalian-derived

<400> SEQUENCE: 5
catctccttg gtgctcaacc                                            20

<210> SEQ ID NO 6
<211> LENGTH: 20
<212> TYPE: DNA
<213> ORGANISM: artificial
<220> FEATURE:
<223> OTHER INFORMATION: Mammalian-derived

<400> SEQUENCE: 6
ctgaagtcga cttggcttgg                                            20

<210> SEQ ID NO 7
<211> LENGTH: 21
<212> TYPE: DNA
<213> ORGANISM: Artificial
<220> FEATURE:
<223> OTHER INFORMATION: Mammalian-derived

<400> SEQUENCE: 7
ctcagatagt ggccagaatg c                                          21

<210> SEQ ID NO 8
<211> LENGTH: 20
<212> TYPE: DNA
<213> ORGANISM: artificial
<220> FEATURE:
<223> OTHER INFORMATION: Mammalian-derived

<400> SEQUENCE: 8
ttgtccaggt gactccaagg                                            20

<210> SEQ ID NO 9
<211> LENGTH: 25
<212> TYPE: DNA
<213> ORGANISM: artificial
<220> FEATURE:
<223> OTHER INFORMATION: Mammalian-derived

<400> SEQUENCE: 9
cgtccgagcc cagaaagatg aggtc                                      25

<210> SEQ ID NO 10
<211> LENGTH: 19
<212> TYPE: DNA
<213> ORGANISM: artificial
<220> FEATURE:
<223> OTHER INFORMATION: Mammalian-derived

<400> SEQUENCE: 10
agaggcgcac gtgagacac                                             19

<210> SEQ ID NO 11
<211> LENGTH: 19
<212> TYPE: DNA
<213> ORGANISM: artificial
```

```
<220> FEATURE:
<223> OTHER INFORMATION: Mammalian-derived

<400> SEQUENCE: 11
tgaagacaat gaagatgtt                                                        19

<210> SEQ ID NO 12
<211> LENGTH: 25
<212> TYPE: DNA
<213> ORGANISM: artificial
<220> FEATURE:
<223> OTHER INFORMATION: Mammalian-derived

<400> SEQUENCE: 12
tttcttttct atgtgctgtt ggtga                                                 25
```